United States Patent
Ts'o et al.

[11] Patent Number: 5,834,185
[45] Date of Patent: Nov. 10, 1998

[54] FORMATION OF TRIPLE HELIX COMPLEXES OF SINGLE STRANDED NUCLEIC ACIDS USING NUCLEOSIDE OLIGOMERS WHICH COMPRISE PYRIMIDINE ANALOGS, TRIPLE HELIX COMPLEXES FORMED THEREBY AND OLIGOMERS USED IN THEIR FORMATION

[75] Inventors: Paul On-Pong Ts'o, Ellicott City; Tina Lynn Trapane, Baltimore, both of Md.

[73] Assignee: Johns Hopkins University, Baltimore, Md.

[21] Appl. No.: 342,647

[22] Filed: Nov. 21, 1994

Related U.S. Application Data

[63] Continuation of Ser. No. 194,731, Feb. 10, 1994, abandoned, which is a continuation of Ser. No. 978,937, Nov. 18, 1992, abandoned, which is a continuation-in-part of Ser. No. 772,081, Oct. 7, 1991, abandoned, Ser. No. 368,027, Jun. 19, 1989, abandoned, and Ser. No. 924,234, Oct. 28, 1986, abandoned.

[51] Int. Cl.[6] ......................................................... C12Q 1/68
[52] U.S. Cl. ............................... 435/6; 436/501; 514/44; 536/25.3; 935/77; 935/78
[58] Field of Search .............................. 435/6, 91.1, 810; 436/501; 514/44; 536/22.1, 23.1, 24.1, 24.3, 24.33, 25.3; 935/77, 78, 88

[56] References Cited

U.S. PATENT DOCUMENTS 4,689,320  8/1987  Kaji .......................................... 514/44
5,422,251  6/1995  Fresco ..................................... 435/91.1

OTHER PUBLICATIONS

Stein et al. (1993) Science, vol. 261, pp. 1004–1012.

Le Doan et al. (1987) Nuc. Acids Res., vol. 15, No. 19, pp. 7749–7760.

Howard et al. (1976) Biochemistry, vol. 15, No. 17, pp. 3783–3795.

New England Biolabs Catalog (New England Biolabs, Beverly, MA, USA, 1986/1987) pp. 60–62.

Kan et al. (1992) FASEB J., vol. 6, No. 1, p. A424.

Ono et al. (1991) J. Am. Chem. Soc., vol. 113, pp. 4032–4033.

New England Biolabs Catalog (1986/1987) (New England Biolabs, Mass., USA) pp. 60–61.

*Primary Examiner*—Ardin H. Marschel
*Attorney, Agent, or Firm*—Cushman Darby & Cushman IP Group of Pillsbury Madison & Sutro

[57] ABSTRACT

Methods of detecting, recognizing or inhibiting or altering expression of a target sequence of a single stranded nucleic acid having any combination of purine and pyrimidine nucleosides by formation of triple helix complexes in conjunction with Second and Third Strands which comprise optionally covalently linked Oligomers are provided.

30 Claims, 15 Drawing Sheets

|  | THIRD STRAND – MOTIF NUMBER | | | | |
|---|---|---|---|---|---|
| TARGET – SECOND STRAND | I | I' | II | II' | III |
| (Par.[1])  (A–Par.[2]) | (A–Par.[3]) | (Par.[3]) | (A–Par.[3]) | (Par.[3]) | (A–Par.[3]) |
| A•ΨU<br>G•ΨiC<br>C•G<br>U(or T)•A | C<br>iC<br>ΨiC<br>T(U) | T(U)<br>iC<br>ΨiC<br>C | T(U)<br>C<br>ΨC<br>iC | iC<br>C<br>ΨC<br>T(U) | A<br>I*<br>iG*<br>G(I) |
| TARGET – SECOND STRAND | III' | IV | IV' | V | V' |
| (Par.[1])  (A–Par.[2]) | (Par.[3]) | (A–Par.[3]) | (Par.[3]) | (A–Par.[3]) | (A–Par.[3]) |
| A•ΨU<br>G•ΨiC<br>C•G<br>U(or T)•A | G(I)<br>I*<br>iG*<br>A | X<br>iI*<br>G<br>2aP | 2aP<br>iI*<br>G<br>X | 9daI<br>I<br>9daA<br>A | A<br>I<br>9daA<br>9daI |

[1] Par. = Parallel
[2] A–Par. = Anti–parallel
[3] Polarity relative to target

Fig. 1

| TARGET – SECOND STRAND | | THIRD STRAND – MOTIF NUMBER | | | | |
|---|---|---|---|---|---|---|
| (Par.¹) | (A-Par.²) | I | I' | II | II' | III |
| | | (A-Par.³) | (Par.³) | (A-Par.³) | (Par.³) | (A-Par.³) |
| A•ΨU | | C | T(U) | T(U) | iC | A |
| G•ΨiC | | iC | iC | C | C | I* |
| C•G | | ΨiC | ΨiC | ΨC | ΨC | iG* |
| U(or T)•A | | T(U) | C | iC | T(U) | G(I) |

| TARGET – SECOND STRAND | | | | | | |
|---|---|---|---|---|---|---|
| (Par.¹) | (A-Par.²) | III' | IV | IV' | V | V' |
| | | (Par.³) | (A-Par.³) | (Par.³) | (A-Par.³) | (A-Par.³) |
| A•ΨU | | G(I) | X | 2aP | 9daI | A |
| G•ΨiC | | I* | iI* | iI* | I | I |
| C•G | | iG* | G | G | 9daA | 9daA |
| U(or T)•A | | A | 2aP | X | A | 9daI |

¹ Par. = Parallel
² A–Par. = Anti-parallel
³ Polarity relative to target

Fig. 2A

| PERMUTATION NUMBER | WATSON•CRICK BASE PAIRS | | | |
|---|---|---|---|---|
| 1 | C•G ⇐ | G•ΨiC ⇒ | U•A ⇌ | A•ΨU ⇋ |
| 2 | C•G ⇐ | U•9daA ⇒ | G•ΨiC* ⇌ | A•ΨU ⇋ |
| 3 | A•ΨC ⇐ | G•ΨiC ⇒ | U•A ⇌ | C•9daG ⇋ |
| 4 | A•ΨC ⇐ | U•9daA ⇒ | G•ΨiC* ⇌ | C•9daG ⇋ |

Fig. 2B

| MOTIF | SECOND-THIRD STRAND BINDING PATTERNS | | | | POLARITY |
|---|---|---|---|---|---|
|  | ⇐ | ⇒ | ⇌ | ⇋ |  |
| CLASS A | | | | | |
| I | ΨiC | iC | T(U) | C | ↑•↓=↓ |
| I' | ΨiC | iC | C | T(or U) | ↑•↓=↑ |
| II | ΨC | C | iC | T(or U) | ↑•↓=↓ |
| II' | ΨC | C | T(U) | iC | ↑•↓=↑ |
| CLASS B | | | | | |
| III | iG* | I* | G(I) | A | ↑•↓=↓ |
| III' | iG* | I* | A | G(or I) | ↑•↓=↑ |
| IV | G | iI* | 2aP | X | ↑•↓=↓ |
| IV' | G | iI* | X | 2aP | ↑•↓=↑ |
| CLASS C | | | | | |
| V | 9daA | I | A | 9daI | ↑•↓=↓ |
| V' | 9daA | I | 9daI | A | ↑•↓=↑ |

Fig. 4
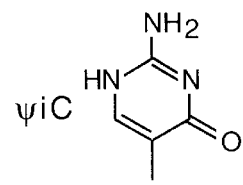 ψiC
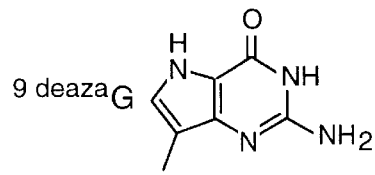 9 deaza G
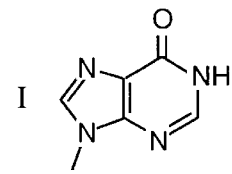 I
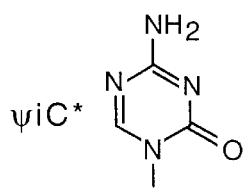 ψiC*
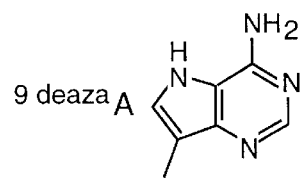 9 deaza A
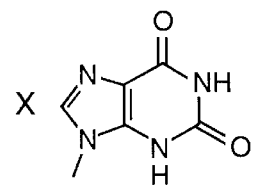 X
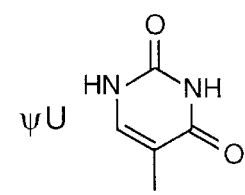 ψU
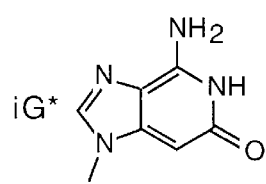 iG*
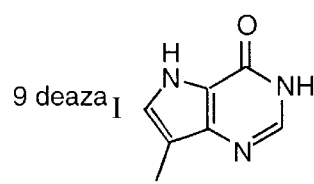 9 deaza I
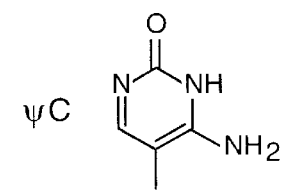 ψC
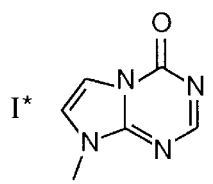 I*
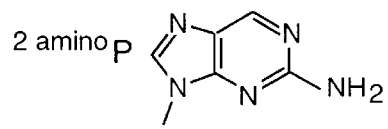 2 amino P
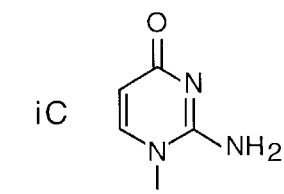 iC
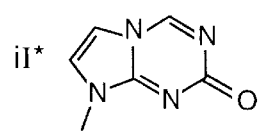 iI*

MOTIF I

MOTIF I'

MOTIF II

MOTIF II'

MOTIF III

Fig. 12
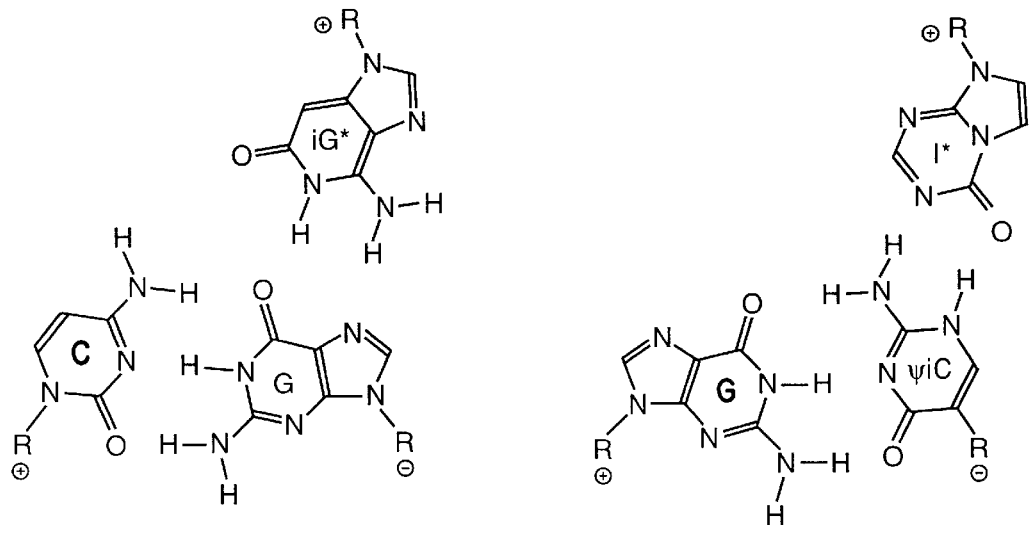
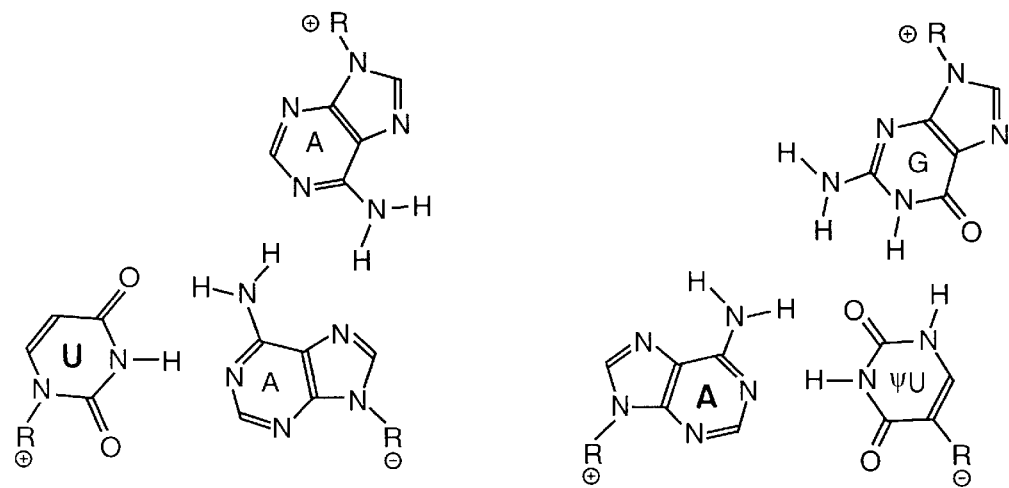
MOTIF III'

MOTIF IV

MOTIF IV'

MOTIF V

MOTIF V'

FORMATION OF TRIPLE HELIX COMPLEXES OF SINGLE STRANDED NUCLEIC ACIDS USING NUCLEOSIDE OLIGOMERS WHICH COMPRISE PYRIMIDINE ANALOGS, TRIPLE HELIX COMPLEXES FORMED THEREBY AND OLIGOMERS USED IN THEIR FORMATION

CROSS-REFERENCE TO RELATED APPLICATIONS

This application is a continuation of application Ser. No. 08/194,731, filed Feb. 10, 1994, now abandoned, which is a continuation of application Ser. No. 07/978,937, filed Nov. 18, 1992, now abandoned, which is a continuation-in-part of U.S. Ser. No. 07/772,081, filed Oct. 7, 1991, now abandoned, which is a continuation-in-part of U.S. Ser. No. 368,027, filed Jun. 19, 1989, now abandoned, which is a continuation-in-part of U.S. Ser. No. 924,234, filed Oct. 28, 1986, now abandoned, the disclosures of which are incorporated herein by reference.

BACKGROUND AND INTRODUCTION TO THE INVENTION

This invention was made with federal governmental support, including grants from the Department of Energy and the NIH/National Cancer Institute, Grant Numbers DE-FG02-B8ER60636 and 2P01CA42762-04AI. The Government has certain rights to this application.

Publications and other reference materials referred to herein are incorporated herein by reference.

The present invention is directed to novel methods of detecting, recognizing and/or inhibiting or altering expression of specific sequences in single stranded nucleic acids, particularly RNA, using Second and Third Strands which are capable of specifically complexing with a selected single stranded nucleic acid sequence to give a triple helix complex.

Formation of triple helix complexes by homopyrimidine oligodeoxynucleotides binding to polypurine tracts in double-stranded DNA by Hoogsteen hydrogen bonding has been reported. See, e.g., Moser, H. E., et al., Science 238:645–650 (1987) and Povsic, T. J., et al., J. Am. Chem. Soc. 111:3059–3061 (1989). The homopyrimidine oligonucleotides were said to recognize extended purine sequences in the major groove of double helical DNA via triple helix formation. Specificity was said to be imparted by Hoogsteen base pairing between the homopyrimidine oligonucleotide and the purine strand of the Watson-Crick duplex. DNA triple helical complexes containing cytosine and thymidine on the third strand have been reported to be stable in slightly acidic to neutral solutions (pH 5.0–6.5), respectively, but have been reported to dissociate on increasing pH. Incorporation of modified bases of T, such as 5-bromo-uracil, and C, such as 5-methylcytosine, into the third strand has been reported to increase stability of the triple helix over a higher pH range. In order for cytosine (C) to participate in the Hoogsteen-type pairing, it was thought that a hydrogen must be available on the N-3 of the pyrimidine ring for hydrogen bonding. Accordingly, it has been proposed that cytosine be protonated at N-3.

DNA has been reported to exhibit a variety of polymorphic conformations; such conformations may be essential for biological processes. Modulation of signal transduction by sequence-specific protein-DNA binding and molecular interactions such as transcription, translation and replication, are believed to be dependent upon DNA conformation. Wells, R. D., et al., FASEB J. 2:2939–2949 (1988).

The possibility of developing therapeutic agents which bind to critical regions of the genome and selectively inhibit the function, replication and survival of abnormal cells is an exciting concept. See, e.g., Dervan, P., Science 232:464–471 (1988). Various laboratories have pursued the design and development of molecules which interact with DNA in a sequence-specific manner. Such molecules have been proposed to have far-reaching implications for the diagnosis and treatment of diseases involving foreign genetic materials (such as viruses) or alterations to genomic DNA (such as cancer).

Nuclease-resistant nonionic oligodeoxynucleotides (ODN) having a methylphosphonate backbone have been studied in vitro and in vivo as potential anticancer, antiviral and antibacterial agents. Miller, P. S., et al. Anti-Cancer Drug Design, 2:117–128 (1987). The 5'-3' linked internucleoside bonds of these analogs are said to approximate the conformation of phosphodiester bonds in nucleic acids. With methylphosphonates, it has been proposed that the phosphate backbone is rendered neutral by methyl substitution of one anionic phosphoryl oxygen, which is thought to decrease inter and intrastrand repulsion due to the charged phosphate groups. Miller, P. S. et al., Anti-Cancer Drug Design 2:117–128 (1987). Oligodeoxynucleoside analogs with a MP backbone are believed to penetrate living cells and have been reported to inhibit mRNA translation in globin synthesis and vesicular stomatitis viral protein synthesis and to inhibit splicing of pre-mRNA in inhibition of herpes simplex virus (HSV) replication. Mechanisms of action for inhibition by the MP analogs include formation of stable complexes with complementary RNA and/or DNA.

Nonionic oligonucleoside alkyl- and aryl phosphonate analogs complementary to a selected single stranded foreign nucleic acid sequence are reported to be able to selectively inhibit the function or expression of that particular nucleic acid without disturbing the function or expression of other nucleic acids present in the cell, by binding to or interfering with that nucleic acid. (See, e.g., U.S. Pat. Nos. 4,469,863 and 4,511,713). The use of complementary nuclease-resistant nonionic oligonucleoside methylphosphonates which are taken up by mammalian cells to inhibit viral protein synthesis in certain contexts, including Herpes simplex virus-1 is described in U.S. Pat. No. 4,757,055.

The use of anti-sense oligonucleotides or phosphorothioate analogs complementary to a part of viral mRNA to interrupt the transcription and translation of viral mRNA into protein has been proposed. The anti-sense constructs can bind to viral mRNA and were thought to obstruct the cell's ribosomes from moving along the mRNA and thereby halting the translation of mRNA into protein, a process called "translation arrest" or "ribosomal-hybridization arrest." Yarochan, et al., "AIDS Therapies", Scientific American, pages 110–119 (October 1988).

The inhibition of infection of cells by HTLV-III by administration of oligonucleotides complementary to highly conserved regions of the HTLV-III genome necessary for HTLV-III replication and/or expression is reported in U.S. Pat. No. 4,806,463. The oligonucleotides were said to affect viral replication and/or gene expression as assayed by reverse transcriptase activity (replication) and production of viral proteins p15 and p24 (gene expression).

The ability of some antisense oligodeoxynucleotides containing internucleoside methylphosphonate linkages to inhibit HIV-induced syncytium formation and expression has been studied. Sarin, et al., Proc. Nat. Acad. Sci. (USA) 85:7448–7451 (1988).

PCT Published Application WO 91/06626 described oligonucleotides which are said to have tandem sequences of inverted polarity and which are said to be useful for forming an extended triple helix with a double helical nucleotide duplex. The inverted polarity was said to stabilize the single strand oligonucleotides to exonuclease degradation.

SUMMARY OF THE INVENTION

The present invention is directed to methods of selectively detecting, recognizing and/or inhibiting or altering expression of a specific target sequence of a single stranded nucleic acid having any selected sequence of nucleosides (e.g., mixed purine and pyrimidine nucleosides) by formation of a triple helix complex wherein a Second Strand specifically binds to the target sequence by Watson Crick base pairing and also specifically hydrogen bonds to a Third Strand. The Second and Third Strands comprise Oligomers that are optionally covalently linked to each other.

Among other factors, the present invention is based upon our finding that triple helix complexes may be formed with a target sequence having any selected combination of pyrimidine and purine bases using the hydrogen bonding motifs described herein. In particular, according to one aspect, nucleosides are used in the Second Strand which have two hydrogen bonding faces, a Watson-Crick binding face and a Second-Third Strand binding face. The Watson-Crick binding face of a Second Strand base hydrogen bonds to the corresponding base of a nucleoside of the target sequence by Watson-Crick base pairing. The Second-Third Stand binding face of a Second Strand base has at least two hydrogen bonding (donor and/or acceptor) sites and specifically hydrogen bonds with and binds to a complementary base of a corresponding nucleoside of the Third Strand. By use of this feature of the two hydrogen bonding faces of the bases of the Second Strand, triplets are formed and formation of multiple triplets gives a triple helix complex. The naturally occurring pyrimidine bases do not have sufficient hydrogen bonding sites on what would be their Second-Third Strand binding faces to stably hydrogen bond with a base of a Third Strand to form a triplet. Since the purine bases, A and G have sufficient hydrogen bonding sites on what would be their Second-Third Strand binding faces, these "open sandwich" type of triple helix complexes were thought to be restricted to pyrimidine-rich target sequences in the absence of other third strand modifications. According to our proposed binding motifs, pyrimidine analogs are provided which have an additional hydrogen bonding (donor/acceptor) site on their Second-Third Strand binding faces ("pyrimidine 5-donor/acceptor bases"). Thus, we have found that by using nucleosides having bases which are analogs of the naturally occurring cytidine and uridine (or thymidine) in the Second Strand in place of those pyrimidines and which, unlike these naturally occurring pyrimidines, have a proton donor or acceptor at the 5-position; both a base of a nucleoside of the target sequence and a base of a nucleoside of the Third Strand can hydrogen bond to the Second Strand base and form a triplet. The base of the corresponding target sequence nucleoside hydrogen bonds with the Watson-Crick binding face of the Second Strand base and the base of the corresponding Third Strand nucleoside hydrogen bonds with the Second-Third Strand binding face of the Second Strand base. Use of these pyrimidine analogs advantageously allows formation of triple helix complexes with single stranded nucleic acids having any target sequence (any mixture of pyrimidine and purine nucleosides) without restriction of the target sequence to homopyrimidine or homopurine sequences or sequences having polypyrimidine or polypurine tracts linked together. Thus, use of nucleosides having pyrimidine 5-donor/acceptor bases in the Second Strand and a Third Strand selected according to one of motifs I to V' of FIG. 1 or FIG. 2B allows formation of a triple helix complex with a target sequence which contains any mixture of pyrimidine and purine bases. In contrast, previously proposed protocols for triple helix formation required either a target sequence having only purine bases or only pyrimidine bases, or if the target sequence was comprised of a mixture of purine and pyrimidine bases, it was thought necessary to use a Third Strand having either lengthening links so as to be able to switch from binding one strand to the other strand or having multiple reverses in strand polarity (e.g., reversing from 5'-3' to 3'-5' and so forth).

According to one aspect, the present invention is directed to a method of detecting, recognizing or inhibiting or altering expression of a specific target sequence of single stranded nucleic acid having nucleosides comprising both purine and pyrimidine bases. The single stranded nucleic acid is contacted with Second and Third Strands which comprise Oligomers optionally linked together. The Second Strand comprises at least one nucleoside with a pyrimidine 5-donor/acceptor base. The Second Strand is sufficiently complementary to the target sequence and the Third Strand is sufficiently complementary to the Second Strand to form a triple helix complex by formation of triplets between individual bases of the target sequence and individual bases of each of the Second and Third Strands.

According to a preferred aspect, the nucleoside sequences of the Second and Third Strands are selected according to one of motifs I to V' of FIG. 1 or FIGS. 2A and 2B such that triplets are formed, each triplet comprising a base of a nucleoside of the target sequence hydrogen bonding with a base of a nucleoside of the Second Strand and the Second Strand base hydrogen bonding with both the target strand base and a base of a nucleoside of the Third Strand. Formation of multiple adjacent triplets produces a triple helix complex.

Thus, according to this aspect, the present invention is based upon our innovative finding that by selecting the base sequences of the Second Strand and the Third Strand according to one of the motifs I to V' of FIG. 1 or FIGS. 2A and 2B one may specifically detect or recognize a target sequence and form a triple helix complex with the target sequence without regard to its base composition. The Second and Third Strands having base sequences selected in accordance with one of motifs I to V' of FIG. 1 or FIG. 2A and 2B exhibit high specificity and high affinity in recognizing the target sequence and formation of a triple helix complex at physiological pH and temperatures.

In one aspect, the present invention provides a Second Strand complementary to the target sequence which binds to the target sequence by Watson-Crick base pairing and which has in place of the naturally occurring pyrimidine bases C and U (or T), modified pyrimidine bases which have an additional hydrogen bonding site at the 5-position ("pyrimidine-5-donor/acceptor-bases"). (See FIG. 3A for the base numbering convention used herein). These pyrimidine-5-donor/acceptor bases have a structure which allows them to act as a proton donor or acceptor at the 5-position of the base's ring and which gives the base an additional position for hydrogen bonding. These pyrimidine-5-donor/acceptor bases have an additional hydrogen bonding site and therefore can form hydrogen bonds and, thus, bind to another base (on its Second-Third Strand binding face) according to one of motifs I to V' of FIG. 1 or FIG. 2B.

These pyrimidine 5-donor/acceptor bases can bind to a base of the target sequence by Watson Crick base pairing on their front side (or "Watson-Crick binding face") and also form hydrogen bonds on their back side (or "Second-Third Strand binding face") with another base according to one of motifs I to V' of FIG. 1 or FIG. 2B (see "Third Strand Base Selection") to form a triplet. Thus, another aspect of the present invention is directed to a Second Strand having at least one pyrimidine-5-donor/acceptor base. Suitable pyrimidine-5-donor/acceptor bases include pseudoisocytosine or pseudoisocytosine* (in place of cytosine) and pseudouracil or pseudocytosine (in place of uracil or thymine). See FIG. 4 for structures.

According to one embodiment, the Second Strand and the Third Strand may be covalently linked and, thus, comprise a single Oligomer. According to an alternate embodiment, the Second Strand and the Third Strand may each comprise separate Oligomers.

According to a preferred aspect, the Second and Third Strands comprise substantially neutral Oligomers. Especially preferred substantially neutral Oligomers are methylphosphonate Oligomers.

Preferably the Second and Third Strands each comprise from about 4 to about 40 nucleosides, more preferably from about 6 to about 30 nucleosides. Especially preferred are Second and Third Strands which each comprise about 8 to about 20 nucleosides.

According to one aspect, the present invention is directed to a Second Strand which is a first Oligomer and which has a nucleoside sequence selected in accordance with one of motifs I to V' of FIG. 1 or FIG. 2A.

According to an alternate aspect of the present invention, a Second Strand capable of forming a triple helix complex with a target sequence having a mixture of purine and pyrimidine nucleosides is provided. The Second Strand comprises a plurality of nucleosides wherein the base portion of each nucleoside has a Watson-Crick binding face capable of binding to a base of a nucleoside of the target sequence by Watson-Crick base pairing and a Second-Third Strand binding face having at least two hydrogen binding sites and being capable of binding to a base of a nucleoside of the Third Strand.

According to another aspect, the present invention is directed to a Third Strand which is a second Oligomer having a nucleoside sequence selected in accordance with one of motifs I to V' of FIG. 1 or FIG. 2B.

Taken together a base of a nucleoside of each of the Second and Third Strands will interact with each other and the base of the Second Strand will interact with a corresponding base of a nucleoside of the target sequence to form a triplet as set forth in one of motifs I to V' of FIG. 1 or FIG. 2A and B. Formation of triplets with bases of multiple adjacent nucleosides of the target sequence result in a triple helix complex.

According to an alternate aspect of the present invention, methods are provided of forming a triplet between a purine nucleoside of a target sequence of a single stranded nucleic acid, a corresponding nucleoside of a Second Stand and a corresponding nucleoside of a Third Stand wherein the Second Strand nucleoside comprises a pyrimidine analog which has a Watson-Crick binding face capable of binding by Watson-Crick base pairing to the purine base and a Second-Third Strand binding face having at least two hydrogen binding sites. The purine nucleoside of the target sequence is contacted with the Second Strand nucleoside and a Third Strand nucleoside which has a base complementary to the Second-Third Strand binding face of the base of the Second Strand nucleoside to give a triplet.

Preferred target sequences for detection, recognition and/or inhibition or alteration of expression by the Second and Third Strands according to the methods of the present invention have from about 4 to about 40 nucleosides. Sequences of this length are long enough to be unique, but are short enough for selectivity towards the target sequence (the Second and Third Strands are unlikely to bind to an unrelated target sequence).

Definitions

As used herein, the following terms have the following meanings unless expressly stated to the contrary.

The term "purine" or "purine base" includes not only the naturally occurring adenine and guanine bases, but also modifications of those bases such as bases substituted at the 8-position, or guanine analogs modified at the 6-position or the analog of adenine, 2-amino purine, as well as analogs of purines having carbon replacing nitrogen at the 9-position such as the 9-deaza purine derivatives and other purine analogs such as those set forth in FIG. 4 herein.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-5-donor/acceptor bases such as are pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'-O-alkyl ribose.

For consistency and in order to avoid confusion we are employing an alternative numbering system for the rings of the pyrimidine and purine analogs used herein so that the number assigned to a ring position will be the same relative to the position on the ring of the C—C or N—C glycosidic bond between the base or base analog and sugar without regard to whether a nucleoside is a C- or a N-nucleoside and without regard to the position of ring nitrogens. This numbering system is based on the numbering used for the naturally occurring pyrimidine and purine N-nucleosides. In the context of the pseudo (Ψ) pyrimidine C-nucleoside, it may be called the "pseudo" (or "Ψ") numbering system, or alternatively just the number of the ring position may be used. The numbering system is shown in FIGS. 3A and 3B wherein each X may be independently nitrogen or carbon.

The term "phosphonate" refers to the group

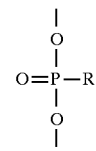

wherein R is hydrogen or an alkyl or aryl group. Suitable alkyl or aryl groups include those which do not sterically hinder the phosphonate linkage or interact with each other. The phosphonate group may exist in either an "R" or an "S" configuration. Phosphonate groups may be used as internucleosidyl phosphorus group linkages (or links) to connect nucleosidyl units.

The term "phosphodiester" refers to the group

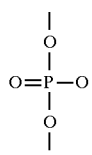

wherein phosphodiester groups may be used as internucleosidyl phosphorus group linkages (or links) to connect nucleosidyl units.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside monomeric units.

The term "oligonucleoside" or "Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/nucleotide polymers wherein one or more of the phosphorus group linkages between monomeric units has been replaced by a non-phosphorous linkage such as a formacetal linkage, a sulfamate linkage, or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

The term "alkyl- or aryl-phosphonate Oligomer" refers to Oligomers having at least one alkyl- or aryl-phosphonate internucleosidyl linkage. Suitable alkyl- or aryl-phosphonate groups include alkyl- or aryl-groups which do not sterically hinder the phosphonate linkage or interact with each other. Preferred alkyl groups include lower alkyl groups having from about 1 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate Oligomer" (or "MP-Oligomer") refers to Oligomers having at least one methylphosphonate internucleosidyl linkage.

The term "neutral Oligomer" refers to Oligomers which have nonionic internucleosidyl linkages between nucleoside monomers (i.e., linkages having no positive or negative ionic charge) and include, for example, Oligomers having internucleosidyl linkages such as alkyl- or aryl-phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, and carbamate linkages. Optionally, a neutral Oligomer may comprise a conjugate between an oligonucleoside or nucleoside/non-nucleoside polymer and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the Oligomer, modify the interaction of the Oligomer with the target sequence, or alter the pharmacokinetic distribution of the Oligomer. The essential requirement is that the oligonucleoside or nucleoside/non-nucleoside polymer that the Oligomer conjugate comprises be neutral.

The term "substantially neutral Oligomer" refers to Oligomers in which at least about 80 percent of the internucleosidyl linkages between the nucleoside monomers are nonionic linkages.

The term "neutral alkyl- or aryl-phosphonate Oligomer" refers to neutral Oligomers having neutral internucleosidyl linkages which comprise at least one alkyl- or aryl-phosphonate linkage.

The term "neutral methylphosphonate Oligomer" refers to neutral Oligomers having internucleosidyl linkages which comprise at least one methylphosphonate linkage.

The term "complementary," when referring to Second and Third Strands, refers to Strands having base sequences which allow the Strand or Oligomer to hydrogen bond with the base sequence of the target sequence of a nucleic acid or another strand and thus bind to the nucleic acid or other strand and in combination to form a triple helix complex.

In the various Oligomer sequences listed herein, "p" as listed in ApG represents a phosphodiester internucleoside linkage and p as in CpG represents a methylphosphonate internucleoside linkage. Also the notation such as T indicates nucleosides linked by methylphosphonate linkages.

The term "triplet" or "triad" refers a hydrogen bonded complex of three nucleoside bases between a base of a target sequence, a base of a first Oligomer and a base of Oligomer as set forth in one of motifs I to V' of FIG. 1.

BRIEF DESCRIPTION OF THE DRAWINGS

FIG. 1 depicts triplet formation motifs using the Watson-Crick pairs of permutation 1 of FIG. 2A.

FIG. 2A depicts four possible permutations of Second Strand bases for use in recognizing the naturally occurring bases of the target sequence. These Second Strand bases have at least two hydrogen bonding positions on their Second-Third Strand binding faces so as to be able to selectively hydrogen bond with a base of a Third Strand nucleoside.

FIG. 2B depicts motifs I to V' for selection of Third Strand bases dependent on the hydrogen bonding pattern of the Second-Third Strand binding face of the Second Strand base.

FIG. 4 depicts the structures of and abbreviation for certain bases used according to the methods of the present invention to form triple helix complexes.

FIG. 12 depicts triads formed with the Watson-Crick base pairs of permutation 1 according to motif III'.

FIG. 12 depicts triads formed with the Watson-Crick base pairs of permutation 1 according to motif IV.

DETAILED DESCRIPTION OF THE INVENTION GENERAL STRATEGY

Figure 3A:
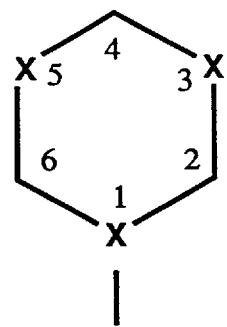
FIG. 3A depicts the numbering system used herein for pyrimidine and pyrimidine analog bases.

The antisense strategy for the development of specifically synthesized oligonucleotides (and their analogs) as sequence-specific/gene-specific therapeutic agents, has now become a major direction for drug development. Two conflicting/contradictory demands in the design of the Second and Third Strands are of primary concern. The therapeutic Second and Third Strands should be absolutely sequence-specific for their designated target sequences in order to avoid unwanted interactions with the large number of other nucleic acid sequences within the cells. Adventitious interactions of administered Oligomers with other sequences could lead to undesirable side effects. In addition, there is a requirement of high affinity of the Oligomers for the target, so that low concentrations for the Oligomers will be sufficient for the masking function at the target site. These two considerations are related to each other in that if the Oligomer's binding to the target nucleic acid is very specific and with high affinity, then the concentration of Oligomer needed for the desired therapeutic effect are reduced and the side effects may become non-existent. This high specificity and affinity is important, especially for systemic treatment when the entire body of the patient is treated with the Oligomers. Additionally, high affinity is significant in that minimum amounts of Oligomers will be required to produce the desired effect, thereby reducing the cost of treating the patient.

Mechanistically, however, high affinity and high specificity are contradictory requirements. In kinetic terms, high affinity requires a very slow or non-existent off-rate once Oligomer and the target are bound to each other. However, a sufficiently high off-rate must exist in order for each Oligomer to search and to determine if the site to which it is bound is completely complementary to its sequence, hence ensuring that the bound site is the correct target site.

Thus, in order for each Oligomer to be highly specific, it must have the ability to search and to determine its complementarity of the interacting site for a perfect match, properties which require a fast off-rate. On the other hand, for the binding to have a high affinity, the Oligomer and the correct target complex with a perfect match must have a very slow off-rate. In all of these processes, the on-rate should be controlled by diffusion and will be influenced by the accessibility of the target sequence of nucleic acid to the Oligomers and only slightly by the size (number of monomeric units) of the Oligomers.

In addition to the strictly chemical and thermodynamic considerations, the kinetic element in living processes is a very vital concern. All of the reactions and interactions in living cells are related to each other functionally in a kinetic manner, and are not necessarily related to each other in a thermodynamic manner. If an inappropriate binding exists too long because of an insufficient off-rate, then damage to the cell may have sufficient time to occur, thus leading to undesirable biological effects. Therefore, on one hand, we need to have a rapid process of search and determination during the initial phase of interaction, but, on the other hand, we need a very slow process of dissociation once the correct binding between the probe and the target nucleic acid occurs.

The above description leads to the next conclusion that for a successful antisense strategy, the interaction between the Oligomers and the target nucleic acid should be a two-step process. The first step is "Search". The major objective in this step is for the Oligomers to rapidly screen interactions with all of the possible nucleic acid targets inside the living cells and tissues as quickly as possible, with a relatively fast off-rate.

After the successful search, which leads to a proper interaction of the Oligomers and the single-stranded target nucleic acid (usually RNA, but it can also be DNA), a second step is now required for the "Sealing", leading to the formation of a complex which has a very slow off-rate. One demonstration of that strategy is in our publications and patent applications which describe utilizing a psoralen derivatized Oligomer. See, e.g., U.S. application Ser. No. 06/924,234 and published PCT Application No. WO 92/02641. In this case, the Oligomer is reasonably short, 10–12 nucleotides in length, and has been derivatized with psoralen which is a photo-reactive crosslinking group. Upon photo-irradiation the psoralen on the Oligomer can form a cyclobutane-type of crosslinking with a double bond in a pyrimidine base, for example, cytosine or uracil located in the target strand only in a perfectly matched duplex. Since the Oligomer will be covalently linked to the target nucleic acid in the perfectly matched duplex upon photo-irradiation, the off-rate is now practically reduced to zero for the covalent complex.

The challenge is to be able to form a similar type of complex in two steps, but to eliminate the requirement for an external energy source, such as photo-irradiation.

Triple Helix Complex Formation With the Target Nucleic Acids

Formation of triple-stranded helices, triple helix complexes or triplexes, in nucleic acid physical chemistry has been reported where a Watson-Crick type of pyrimidine:purine duplex has a pyrimidine third strand bound in its major groove using Hoogsteen-type base pairing as the motif for the base triad. The most well known case is the T•A=T$^{1/}$ (or U•A=U) base triad, as well as the C•G=C+ triad. In this situation, T•A=T or U•A=U can be formed at neutral pH, or without additional contribution by protonation. On the other hand, in the system of C•G=C+, protonation on the third strand of C is required. Therefore, the formation of such triplexes is sensitive to pH changes around neutrality. We have determined alternative compounds which can be used in place of C for triple helix formation which has eliminated this requirement (protonation of C). One such compound is the pseudo-isocytosine nucleoside. With these alternative bases, an appropriate hydrogen-bonding site is provided in the neutral unprotonated base for triple helix formation. The use of pseudoisocytosine in the third strand to form triple helix complexes is described in our co-pending application, U.S. application Ser. No. 07/772,081.

[1] In T•A=T, "•" refers to the Watson Crick base pairing between the single stranded target (in bold) and Second Strand (or taken together double stranded target) and "=" refers to the pairing with the Third Strand.

In that application, we have outlined two possible arrangements for triple helix construction with the target nucleic acid as one strand, and with two Oligomers as the Second and Third Strands in the triple helix complex, the "closed sandwich" and the "open sandwich". The "closed sandwich" arrangement can be formed when the target sequence consists only of purine residues and involves the binding of a homopyrimidine Oligomer as a Second Strand as a Watson-Crick complement to one side of the target strand (at the C6, N1, C2 face of the purine base) and another Oligomer as a Third Strand binding to the other side of the target strand's purine bases which offer two hydrogen-bonding sites (the C6, N7 face) in the major groove. In this case, each Oligomer participates in sequence specific hydrogen-bonding with the target strand and the Oligomers (Second and Third Strands) do not participate in hydrogen-bonding with each other; i.e. the target sequence is enclosed by hydrogen-bonding interactions with the Oligomers. This type of arrangement is termed a closed triplex or "closed sandwich" because the target sequence is sandwiched between two Oligomers. The "open sandwich" arrangement using naturally occurring bases can be formed when the target sequence consists only of pyrimidine residues. Here sequence specific Watson-Crick interactions are satisfied by a homopurine Oligomer (Second Strand). However, in order for triple helix formation to occur, this Second Strand must interact with a Third Strand at its C6, N7 face. In this case only the Second Strand makes sequence specific hydrogen-bonds with the target sequence and the Second and Third Strands share a hydrogen-bonding interface and hydrogen bond with each other. In this option, the target strand is on an open side of the triple helix complex. This second type of arrangement is termed an open triple helix or "open sandwich".

From theoretical considerations involving short nucleic acid target sequences, it is possible that for dissociation of the target nucleic acid, after triple helix formation, so that it is completely free of interactions with uncomplexed Oligomers, a closed sandwich may be a more favorable arrangement than an open sandwich. This understanding is somewhat intuitive as the target strand must break away from two sets of hydrogen-bonding interactions with the Oligomers in the closed sandwich case, whereas there is only one such set of interactions to break in the open sandwich case. However, this consideration may not be relevant when the target nucleic acid is a large molecule with only a small segment of the target sequence in a single-stranded form, and, thereby, available for sequence-specific complex formation. For such a large molecule plus small Oligomer interaction, the entropy considerations strongly favor dissociation of the complex due to the departure of the small Oligomer from the larger nucleic acid molecule. In this case, the closed sandwich may not have any advantage over the open sandwich, and may even be more sterically hindered than the open sandwich. Therefore, for the complex formation between a large target nucleic acid and small Oligomers, the open sandwich arrangement may be preferred. In this case, the Second Strand is bound as the Watson-Crick complement to the target sequence and is restricted from dissociating by the added Third Strand. This Third Strand binding may decrease the dissociation constant of the complex by 100 to 1000 fold, and could reduce the needed concentration for therapeutic action, for instance, from 100 $\mu$M to 1.0 or 0.1 $\mu$M. More importantly, the length requirement for the available open sequence of the target nucleic acid can still be relatively short, such as from 10 to 14 nucleotide units. The target nucleic acid is much more likely to have an open single-stranded region of such a length, instead of a longer ($\leq 20$ nucleotides) sequence.

Additional theoretical considerations for not using long Second and Third Strands are described in Ts'o, et al., Annual, NY Academy of Sciences, in press (to be published 1992).

Sequence Restriction in Triple Helix Formation

The reported strategies involved in triple helix formation at specific target sites, and the ability to have a workable antisense therapeutic application through triple helix formation, has been greatly limited by the requirement of the homopurine or homopyrimidine sequence. Simply stated, until now we were unable to form stable sequence-specific triple helixes without having the single-stranded nucleic acid target consisting of only purines or only pyrimidines. The present invention provides a breakthrough related to this restriction, i.e., triple helix complexes may be formed with any sequence arrangement of the single-stranded nucleic acid target.

The major limitation in the triple helix formation has been that the pyrimidine in the Watson-Crick duplex has only one additional hydrogen bonding site after the formation of the duplex via Watson-Crick hydrogen bonding scheme. One aspect of the present invention is to use C-nucleosides for the pyrimidines in the Second Strand of the Watson-Crick duplex formed with the target sequence in replacement of the naturally occurring N-nucleoside. With the C-nucleosides, the glycosidic bond between the pyrimidine base and the sugar moiety is a carbon—carbon bond, whereas with the N-nucleosides, the pyrimidine base and sugar are attached by a nitrogen—carbon bond. In such a manner, the C-pyrimidine nucleoside has an additional hydrogen bonding site for a pair of hydrogen bond formation with the third strand added to the Watson-Crick duplex. Since there is only a small change in the C—C bond vs. the C—N bond distance (about 0.1 Å), the original nucleic acid structure is preserved with minimal perturbation. In this manner, the usefulness of C-pyrimidine nucleosides is greatly magnified for a triple helix formation as compared to the naturally occurring N-pyrimidine nucleoside.

Accordingly, the present invention provides a comprehensive approach for triple helix formation with target nucleic acid sequences consisting of any combination of the four naturally occurring bases which is described below. The bases of some of the nucleosides proposed for use in the Second and Third Strands are naturally occurring minor bases, such as pseudo-uracil, and xanthine and are commercially available; syntheses for other of the unusual bases have appeared in the literature; and yet other may be prepared by syntheses analogous to literature syntheses. (See included references given in "Nucleoside Bases" herein below). FIGS. 7 to 16 depict triads formed according to motifs I to V' of FIG. 1 (or Permutation 1 of FIG. 2A).

Second Strand—Preferred Pyrimidine-5-Donor/Acceptor Bases

As noted the Second Strand incorporates in place of the naturally occurring cytidine or uridine (or thymidine) nucleosides, analogs of these nucleosides which are able to form Watson-Crick base pairs with the target sequence, but also have an additional hydrogen bonding site at the position which corresponds to the 5-position of cytidine or uridine, which we have termed pyrimidine-5-donor/acceptor bases nucleosides.

Preferred pyrimidine-5-donor/acceptor bases nucleosides include C-nucleosides, that is where the glycosidic bond is attached to a carbon atom of the heterocyclic base, rather than to a ring nitrogen. Attachment to a carbon atom allows the ring nitrogen to be available for hydrogen bonding.

Figure 3B:
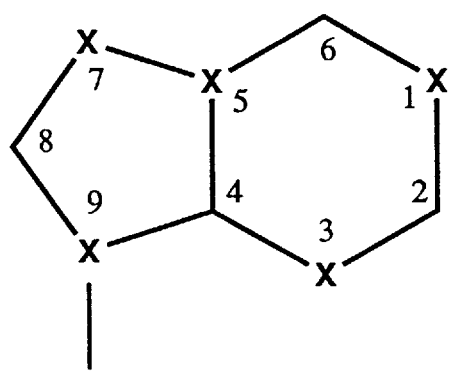
FIG. 3B depicts the ring numbering system used herein for purine and purine analog bases.
Figure 5:
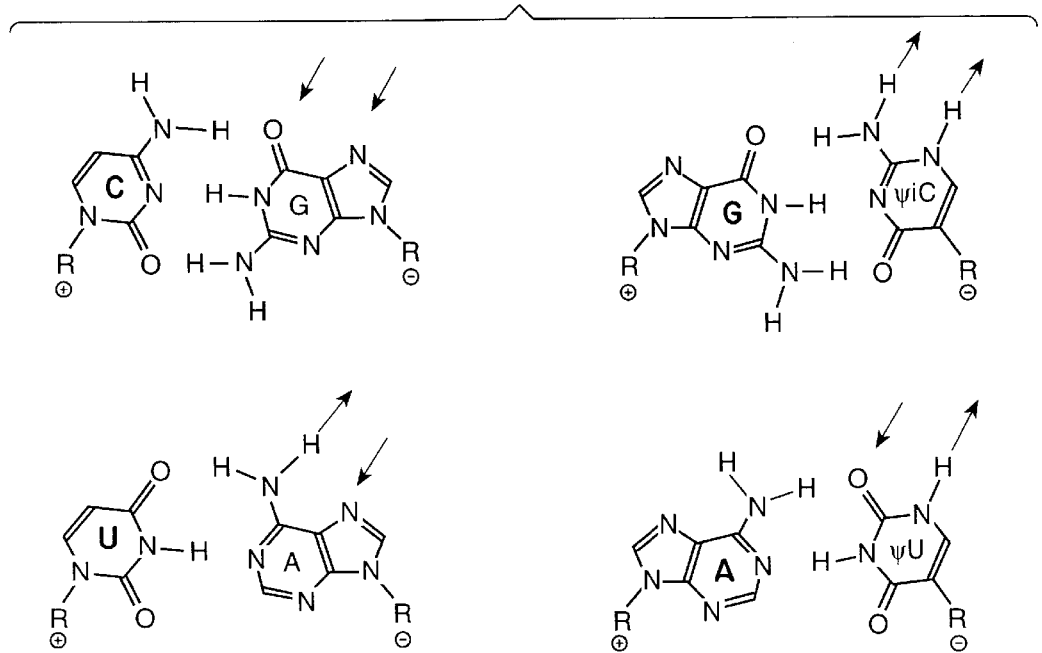
FIG. 5 depicts the Watson-Crick base paring schemes for permutation 1 of FIGS. 2A.
Figure 6:
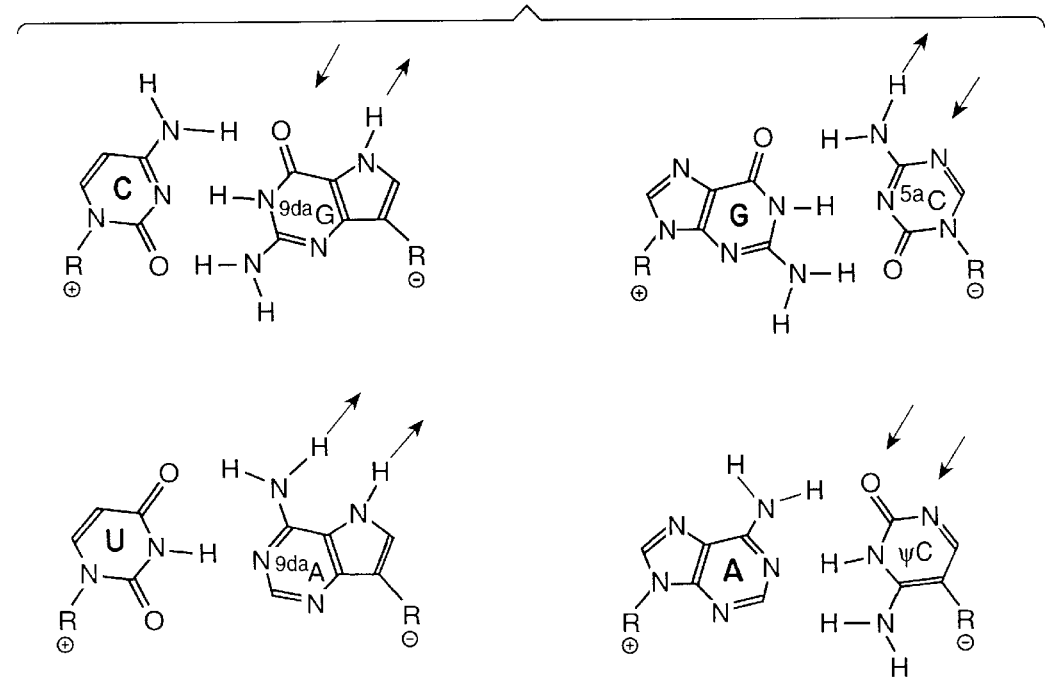
FIG. 6 depicts the Watson-Crick base pairing schemes for permutation 4 of FIG. 2A.
Figure 7:
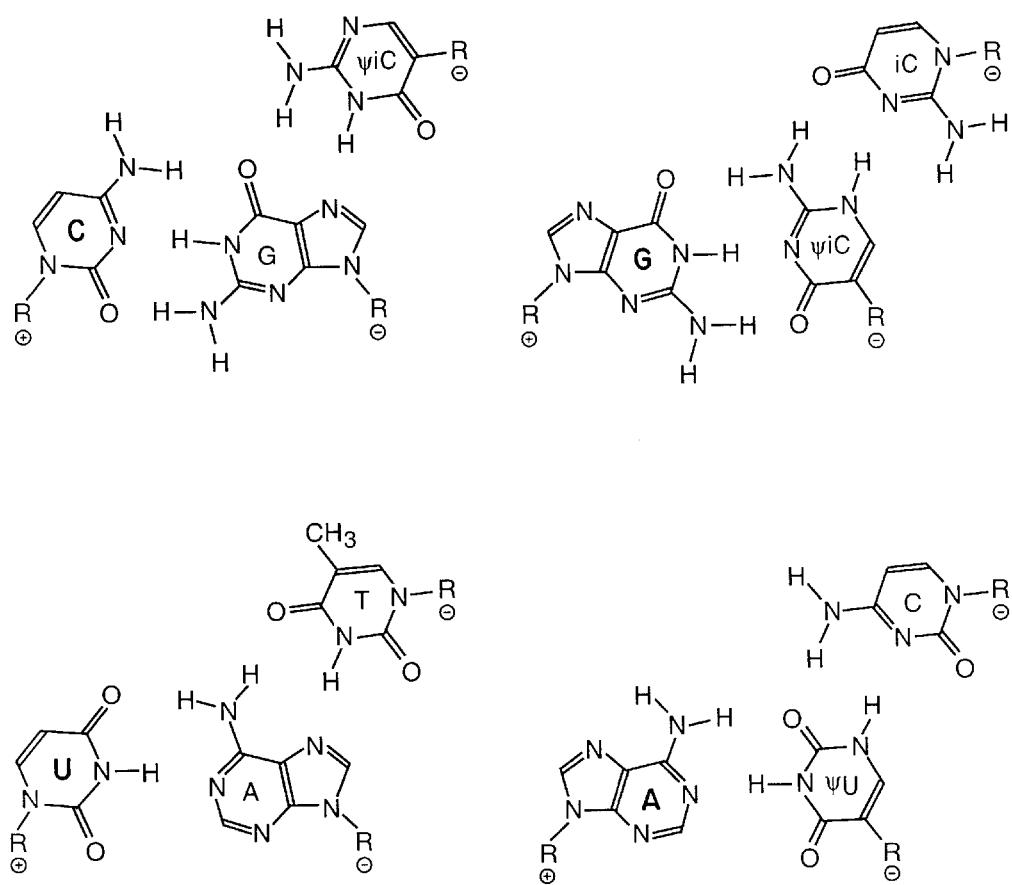
FIG. 7 depicts triads formed with the Watson-Crick base pairs of permutation 1 according to motif I.
Figure 8:
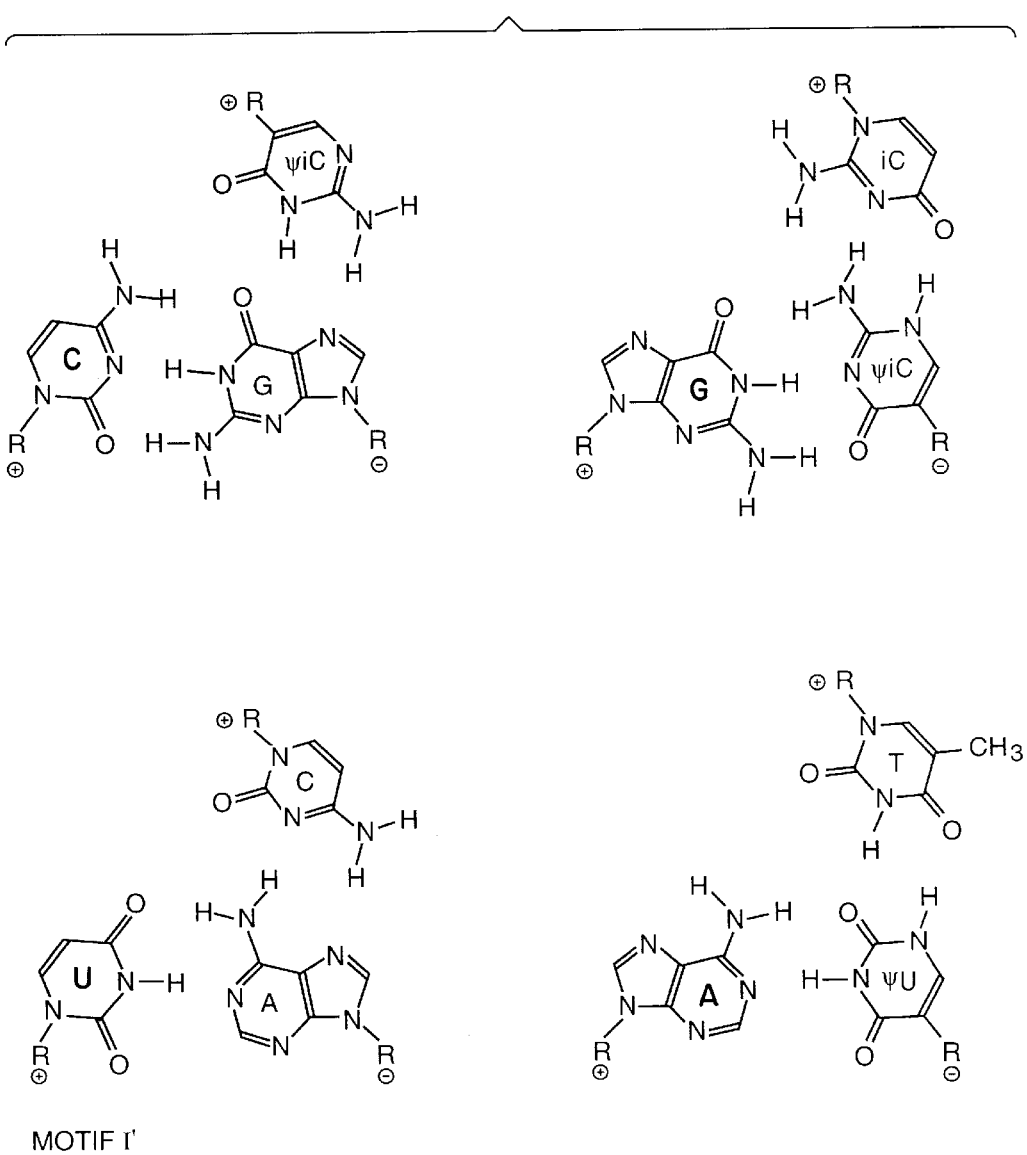
FIG. 8 depicts triads formed with the Watson-Crick base pairs of permutation 1 according to motif I'.

The proposed hydrogen bonding patterns and isomorphic geometries requires the use of several nonstandard (i.e. not naturally occurring) heterocyclic bases. We have adopted a numbering format for all the nucleosides based on the numbering format used for the naturally occurring purine and pyrimidine nucleosides. The atom numbering for the naturally occurring purine and pyrimidine nucleosides is set forth in FIGS. 3A and 3B. For nucleosides with an N-glycosidic linkage to the sugar, the atom numbering follows that for the standard bases. For these bases the covalent attachment to the sugar is at the N9 position for purines and at N1 for pyrimidines. Under conventional numbering guidelines the numbering for the C-nucleosides in relation to the glycosidic bond would be different due to the different positioning of the heterocyclic nitrogens in relation to the glycosidic bond. In order to avoid confusion due to these differences in numbering, we are employing an alternative numbering system for the C-nucleosides ($\Psi$-pyrimidines) in this application (see FIG. 3A). This "pseudo" numbering system allows the position of hydrogen bonding sites on the C-nucleosides to be analogous to the standard bases in relation to the glycosidic bond. Thus, pseudouridine will have hydrogen bonding acceptors at the $\Psi O2$ and $\Psi O4$ positions. Note that this hydrogen bonding pattern is the same as for the standard uridine nucleoside except for the additional donor site at the $\Psi N5$ position.

Four different permutations of the four Watson-Crick type base pairs which form the basis of the triple helix formation motifs are depicted in FIGS. 2A and 2B. The binding motifs using preferred permutation 1 are further tabulated in FIG. 1. In FIG. 1, target sequence and Second Strand bases in each pair are on the left and right, respectively, with glycosidic linkages and the minor groove oriented downward. Strand polarity is indicated at the C1' position.

For purposes of these figures, the target strand base will be indicated first in bold with the complementary base in the Second Strand separated by a bullet (•) representing Watson-Crick hydrogen bonding schemes in each pair. Recognition of target sequence pyrimidine bases by Second Strand bases gives the standard base pairs C•G and U•A. According to a preferred embodiment, recognition of target sequence purine bases is accomplished by C-nucleoside pyrimidine bases on the Second Strand to give the base pairs, G•$\Psi$iC and A•$\Psi$U. The hydrogen bonding pattern for these "pseudo Watson-Crick" base pairs is the same as for the standard G•C and A•U base pairs. However, by use of these pyrimidine-5-donor/acceptor bases in the Second Strand there is a pair of hydrogen bonding donor/acceptor sites in the major groove of the double helix at the pyrimidine base on the Second Strand, an additional site for hydrogen bonding is provided at •N5 of each C-nucleoside at a position approximately isomorphous to N7 of the purines in the C•G and U•A base pairs. The four base pairing schemes (target•Second Strand) each have a unique pattern of hydrogen bond donors and acceptors on the Second Strand on the back side facing the major groove (i.e., on the Second-Third Strand binding face). Specifically, C•G has two acceptors, G•$\Psi$iC has two donors, U•A has a donor and an acceptor (as viewed from the major groove) and A•$\Psi$U has an acceptor and a donor. Use of these unique patterns of hydrogen bonding sites on the bases of the Second Strand for the four target bases make it possible to construct a series of isomorphic base triad motifs.

Third Strand Base Selection

Selection of nucleosides (or bases) for the Third Strand may be based on one of triad motifs I to V' of FIGS. 1 and 2B. These motifs are based upon Third Strand recognition by either pyrimidine or purine nucleosides and are separated into three classes according to their general recognition schemes. Systematic construction and ordering of these motifs will be according to the following set of guidelines. First, it is assumed that all nucleosides on the Third Strand will have the anti configuration of the base at the glycosidic linkage. Therefore, proposed Third Strand polarities can be made directly by comparison to the Watson-Crick strands. Second, a pair of specific hydrogen-bonds must be made to the Watson-Crick Second Strand by adjacent donor/acceptor sites on the Third Strand base. As discussed in detail below, pyrimidine bases possess two sets of adjacent sites (C4-N3 and N3-C2) whereas purine bases have three (C6-N1, N1-C2 and C6-N7). Third, the overall form of the base triads should be geometrically isomorphous. Because the target strand may contain a heterologous sequence of bases, the Watson-Crick section of the base triads will have the familiar pseudo dyad symmetry of the base pair. However, due to the differences in shape of the pyrimidine and purine bases, the third strand may be only of one type of base (i.e., all pyrimidine or all purine). This requirement is important to the formation of triple-stranded helices in order to ensure regular positioning of the Third Strand backbone and to optimize stacking interactions between adjacent triads.

Figure 9:
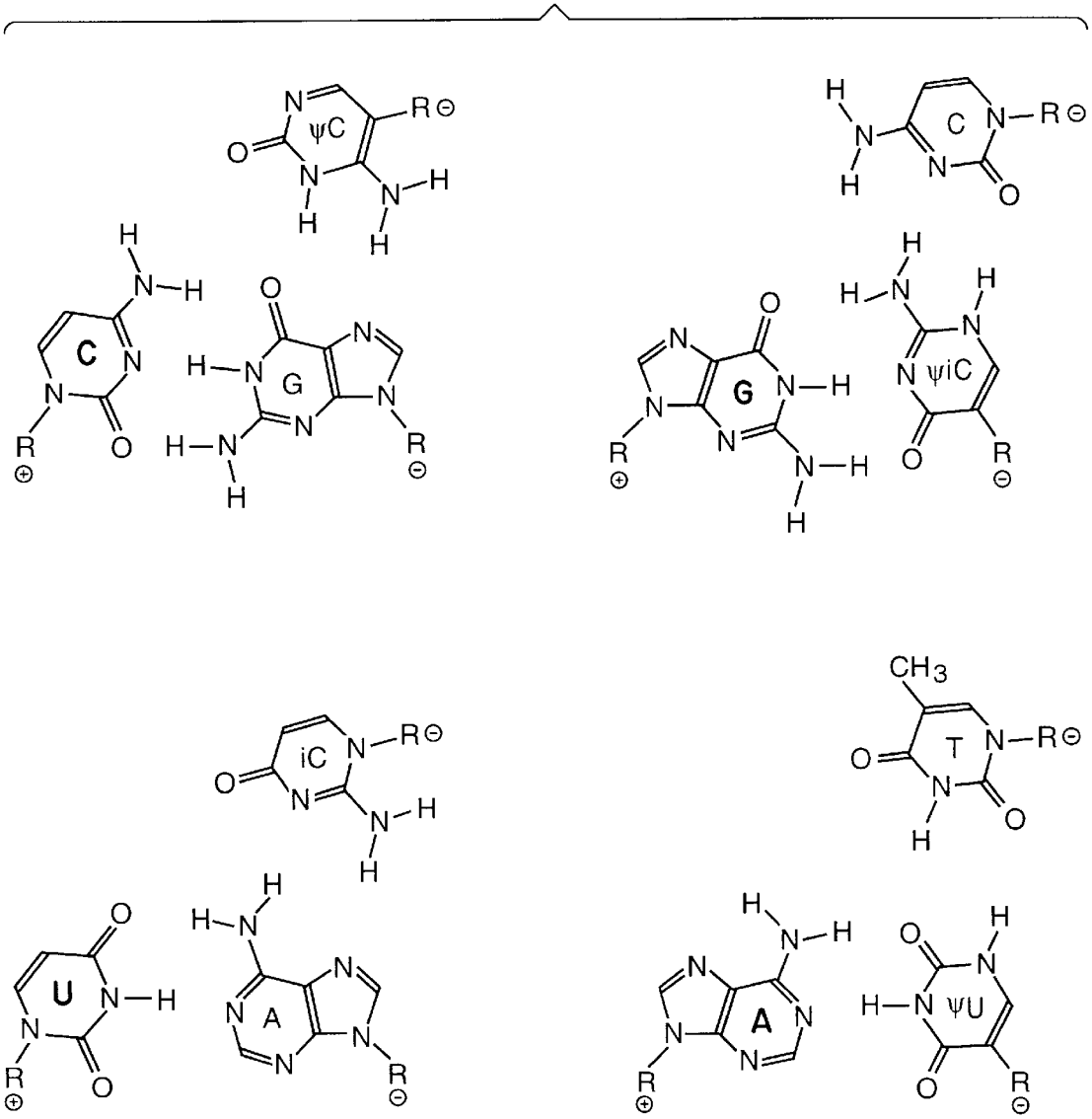
FIG. 9 depicts triads formed with the Watson-Crick base pairs of permutation 1 according to motif II.
Figure 10:
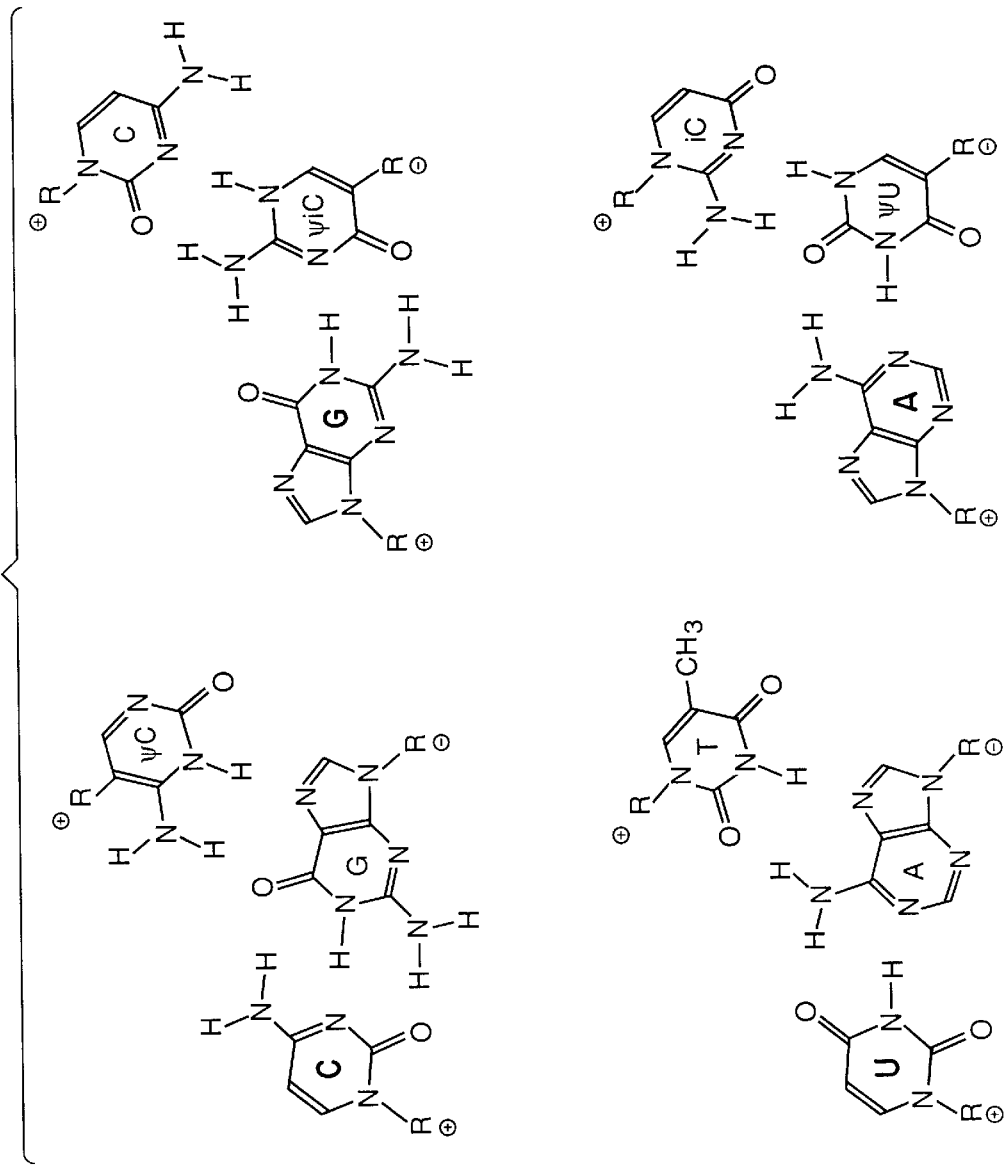
FIG. 10 depicts triads formed with the Watson-Crick base pairs of permutation 1 according to motif II'.
Figure 11:
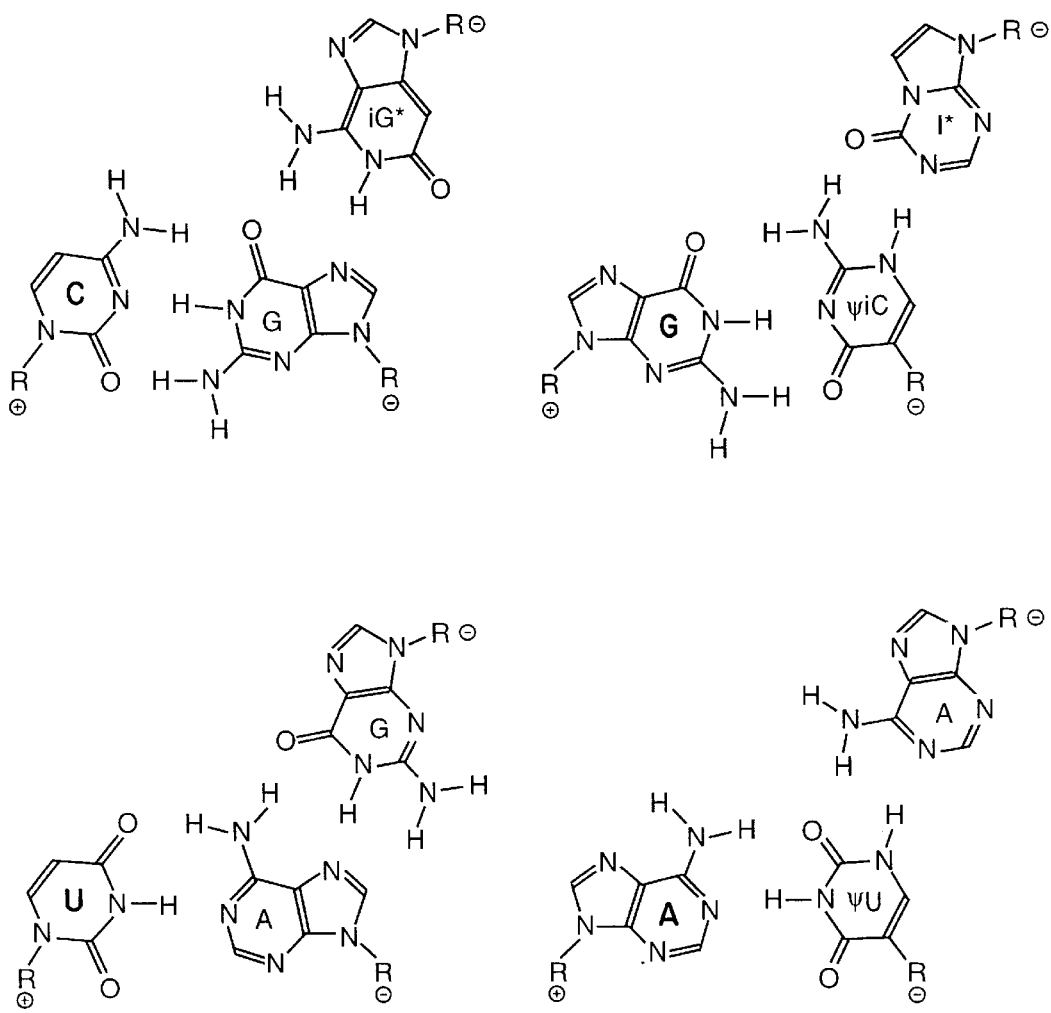
FIG. 11 depicts triads formed with the Watson-Crick base pairs of permutation 1 according to motif III.
Figure 13:
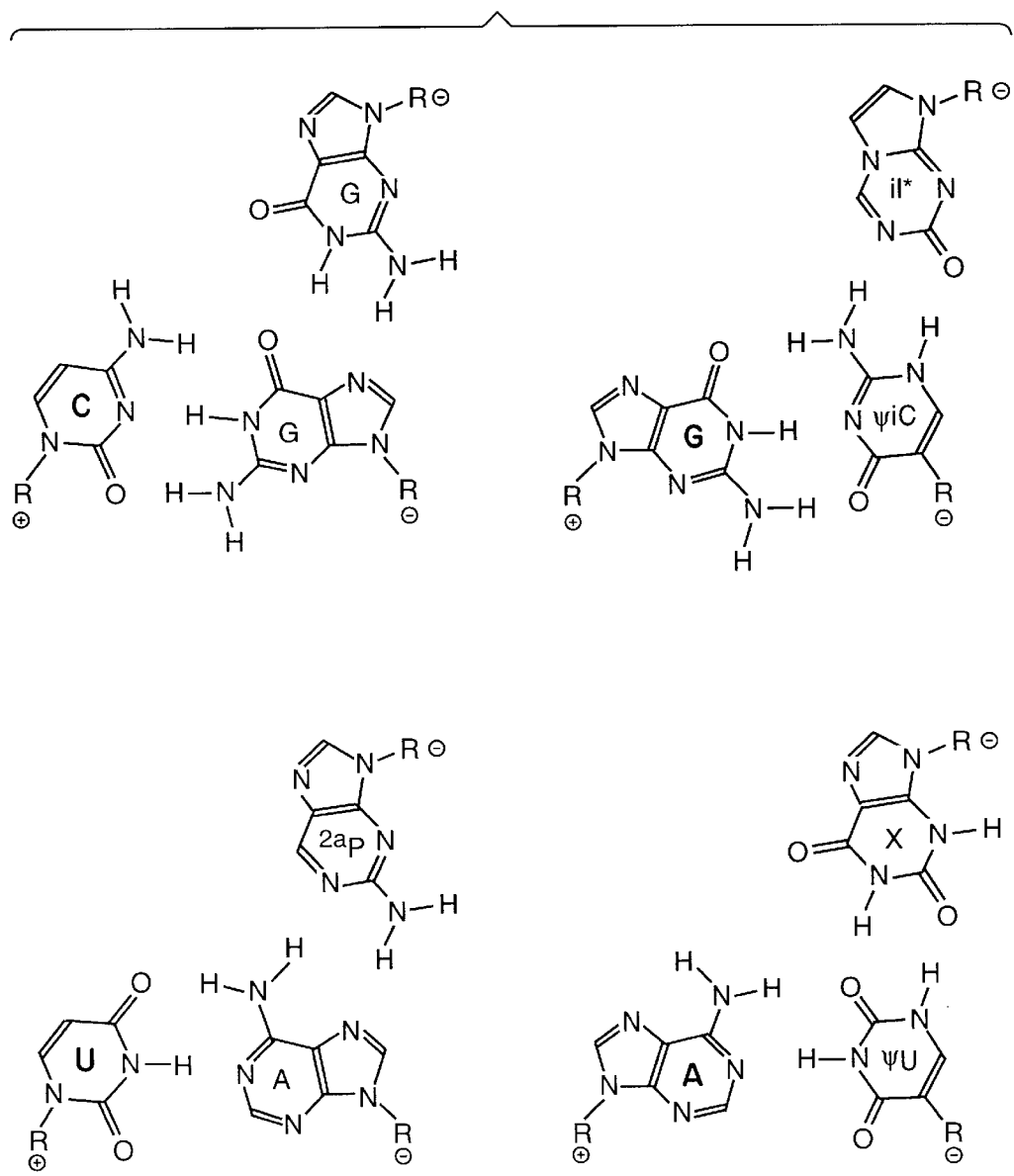
Figure 14:
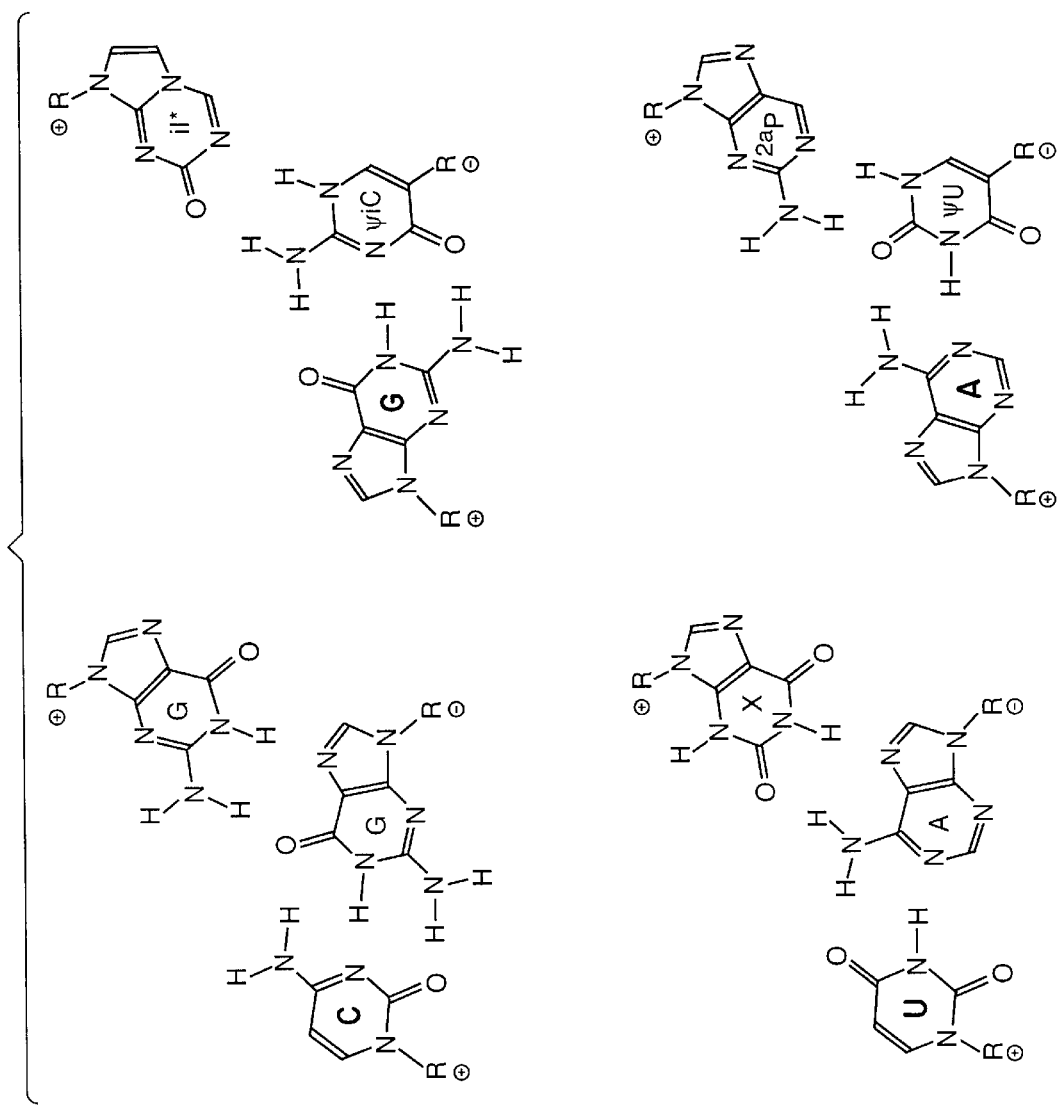
FIG. 14 depicts triads formed with the Watson-Crick base pairs of permutation 1 according to motif IV'.
Figure 15:
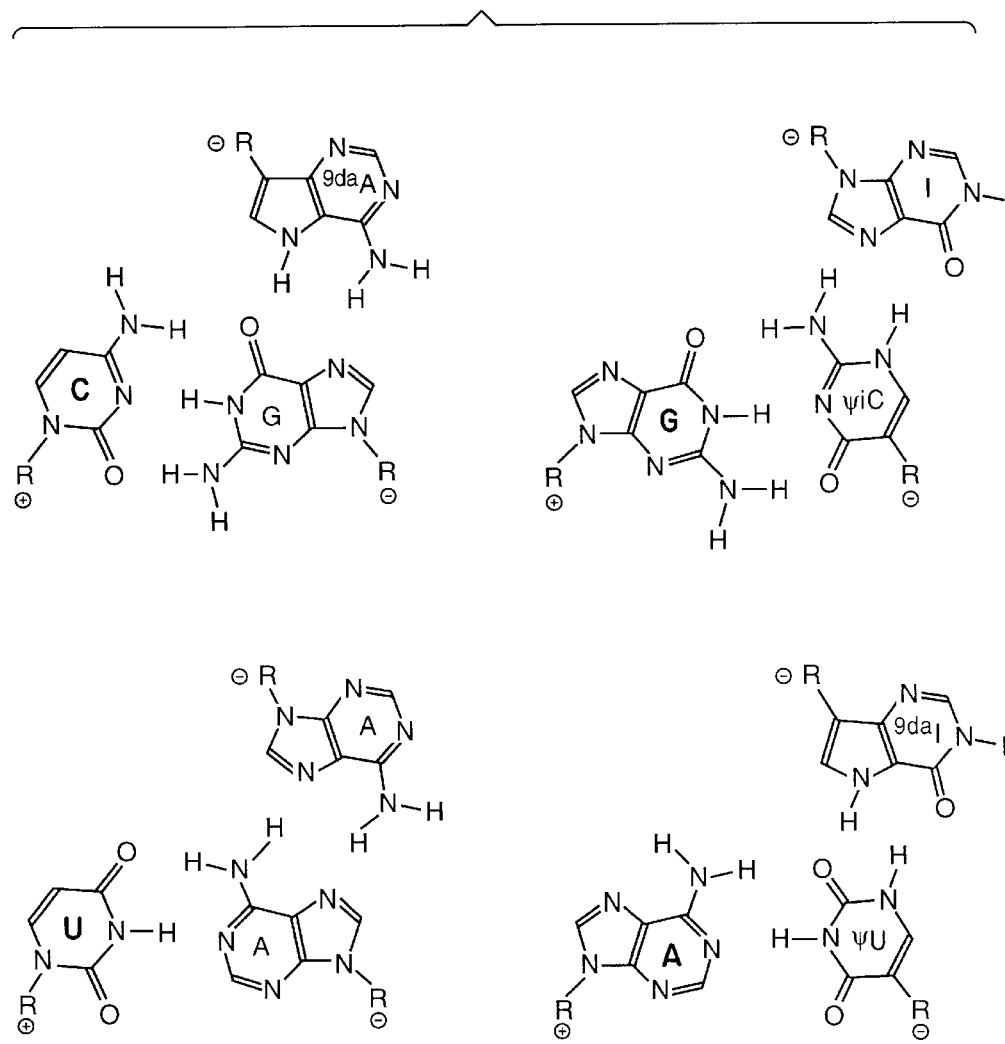
FIG. 15 depicts triads formed with the Watson-Crick base pairs of permutation 1 according to motif V.
Figure 16:
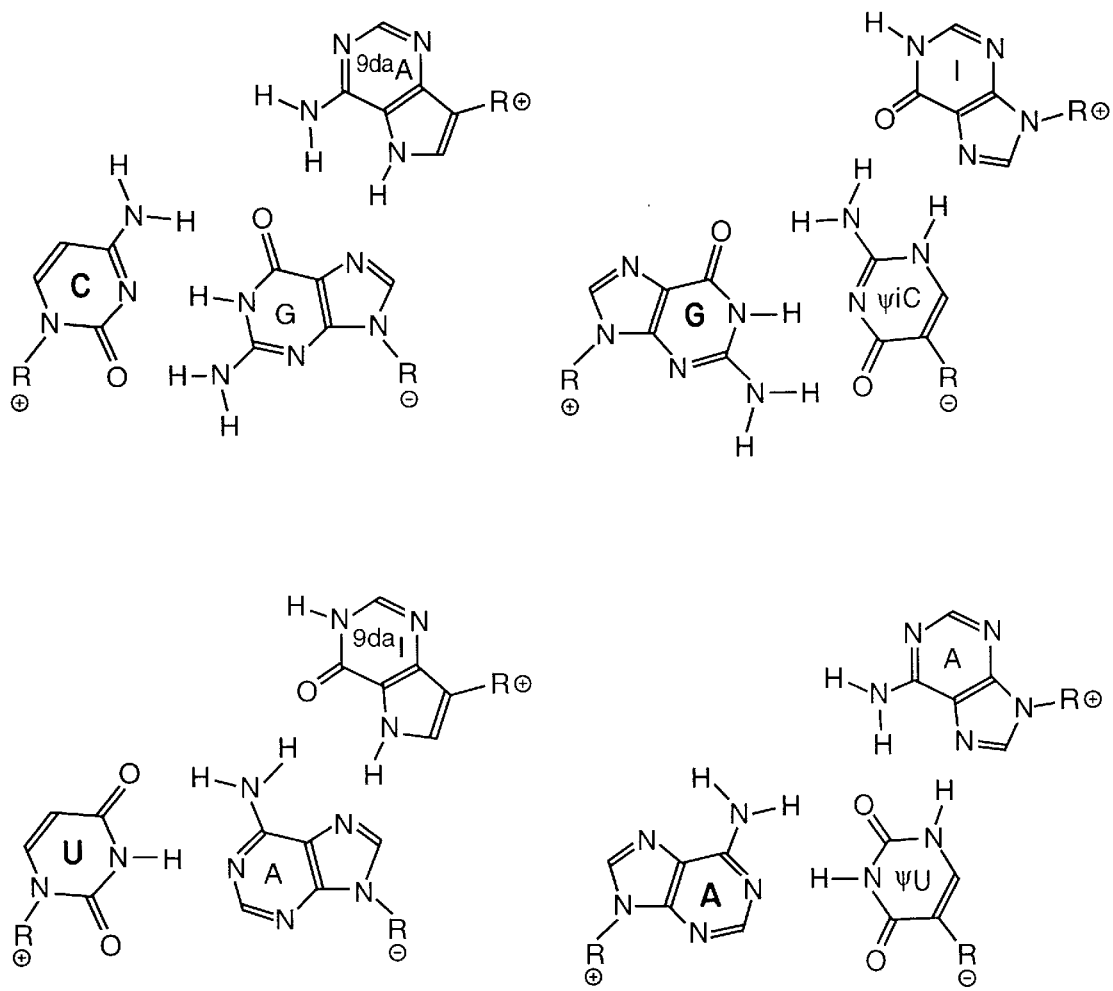
FIG. 16 depicts triads formed with the Watson-Crick base pairs of permutation 1 according to motif V'.

Motifs I, I', II and II' (Class A motifs) are constructed using pyrimidine Third Strand bases. Motif I is based upon the most well known base triad, T•A=T (analogous to U•A=T). Here the Third Strand T (at O4 and H3) accepts and donates a hydrogen-bond to A (at H6 and N7). This type of hydrogen-bonding scheme was first identified by Hoogsteen in crystals of 1-methylthymine and 9-methyladenine. The strand polarities of triple helices containing only this triad has been shown to be antiparallel for the Watson-Crick interaction and parallel for the Hoogsteen interaction. The isomorphic triads in this motif are generated by identifying pyrimidine bases which possess the requisite hydrogen-bond donor/acceptor pairs at C4 and N3 or at comparable position in $\Psi$-pyrimidines. Recognition of the Second Strand at G requires two donors on the Third Strand. This is provided by the $\Psi$iC base (note that the tautomeric form is now different than that required for Watson-Crick recognition by this base) or alternatively the $\Psi$iC* base. The following discussion is directed to permutation 1 of FIG. 2A which is more fully depicted in FIG. 1. The individual triads of motifs I to V' for permutation 1 are depicted in FIGS. 7 to 16. Recognition of Second Strand $\Psi$iC requires two acceptors provided by the natural base analog iC. The triad completing motif I involves recognition of $\Psi$U by C which provides a donor and acceptor (again, as viewed from the major groove of the Watson-Crick helix). Motif I' is related to motif I by an inversion of the polarity of the Third Strand backbone, maintaining Third Strand recognition by donor-acceptor sites at C4 and N3 positions of the Third Strand pyrimidine bases. Therefore, base pairing involving two donors to two acceptors (C•G←ΨiC or G•ΨiC→iC) can be constructed by flipping the orientation of the base (thereby the orientation of the backbone) for motif I 180° in the plane of the paper so that the donor/acceptor at N3 (or ΨN3) is now hydrogen-bonding at the site on the Second Strand base closest to the major groove and the substituent at C4 (or ΨC4) is now hydrogen-bonding toward the minor groove. Such a rotation of the bases in motif I for the U•A=T or A•ΨU=C triads will result in mispairing. However, an interchange of the Third Strand bases allows the correct hydrogen-bonding patterns to be made, resulting in the triads U•A=C and A•ΨU=T for motif I'. (See FIG. 8). Construction of the triads for motif II involves recognition of the Second Strand base by N3 and C2 of the Third Stand pyrimidine bases. As for motif I, the Third Strand is parallel to the strand to which it binds. The base triads C•G=ΨC, G•ΨiC=C, U•A=iC and A•ΨU=T as shown in FIG. 9 are proposed. Motif II' is related to motif II by similar rules interconverting motifs I and I'. Here it should be noted that the following triad of motif II':U•A=T involves an A=T hydrogen bonding scheme of the type also found in crystals of thymine and adenine known as reverse Hoogsteen. (See FIG. 10).

It should be noted that the proposed base triad motifs include a subset which can be utilized to recognize naturally occurring double-stranded target pyrimidine•purine sequences. The base pairs C•G and T•A found in DNA are equivalent to the third and fourth Watson-Crick pairs in each motif (See FIG. 1). Therefore, it may be possible to form triple-stranded helices at double-stranded target sites by the addition of a single oligomer probe designed according to the rules of the ten motifs presented here. For example, it was described in U.S. application Ser. No. 07/772,081, filed Oct. 7, 1991 of which the present application is a continuation-in-part, that a synthetic oligonucleotide probe containing ΨiC and U residues may bind sequence specifically to a homopyrimi-dine•homopurine target sequence, forming a triple-stranded complex according to motif I. Other examples of pyr•pur=pur triple helices formed from homopolymer sequences have been reported. The C•G=G triple helix first reported by Lipsett, M. N., J. Biol. Chem. 239:1256–1260 (1963), may form according to either motif IV or IV', although the recent studies on intramolecular complexes, which forces the two purine strands to be antiparallel, seems to indicate that motif IV' is the preferred pur=pur interaction.

In general, base substitutions may be made in any motif as long as the specific hydrogen bonding patterns are maintained and the new triad remains isomorphic to the remaining triads in the motif. For instance, Third Strand recognition by purine bases in motifs III, III', IV and IV' does not involve hydrogen-bonding at N7. (See, e.g., FIGS. 11 to 14). Therefore, it may be advantageous to synthesize some or all of the Third Strand residues as 7-deaza- analogs (derivatives of tubercidin) in order to avoid unwanted interactions at this face of the Third Strand. In addition, the sugar moiety and backbone linkages of the Oligomer probe strands can be any that are available. The choice of these elements for the backbone should be made based upon their ability to confer chemical stability and favorable characteristics in terms of binding stability and specificity. Obviously, a number of choices are available regarding both sugar and backbone linkage. Common sugar moieties include 2'-deoxyribose, ribose, or 2'-O-methylribose. Suitable backbones for the Third Strand include phosphodiester, methylphosphonate or phosphorothioate.

B. FIGS. 2A and 2B

The binding motifs set forth in FIG. 1 plus three other permutations of Second Strand recognition schemes having Watson-Crick complementarity to the four naturally occurring target strand bases and also having unique hydrogen bonding patterns on their Second-Third Strand binding faces for Third Strand recognition are set forth in FIG. 2A.

In FIG. 2B, the hydrogen bonding patterns for the Second-Third Strand binding face are depicted by the double arrow or pair of arrows to the right of the Second Strand base. For Third Stand base recognition using two hydrogen bonds, four hydrogen bonding patterns are possible. These patterns are indicated as follows: →represents two donor sites, ←represents two acceptor sites, ⇌represents a donor and an acceptor site in a specific orientation, and ⇌represents an acceptor and a donor site in a specific orientation. The triads for motifs I to V' using Second Strand bases selected according to permutation 1 of FIG. 2A and Third Strand bases selected according to motifs I to V' are depicted in FIGS. 7 to 16.

FIG. 2B depicts the Third Strand binding motifs for each of the four specified Second-Third Strand binding patterns. Strand polarity of target, Second and Third strand are indicated in the right hand column.

Base sequences for appropriate Second and Third Strands to form a triple helix complex with a target strand having any combination of pyrimidine nucleosides may be conveniently determined using FIGS. 2A and 2B.

Second and Third Strands

The Second and Third Strands may comprise separate Oligomers. Alternatively, the Second and Third Strands may be covalently linked together.

Preferably the Second and Third Strands each comprise from about 4 to about 40 nucleosides, more preferably from about 6 to about 30 nucleosides and especially preferred are Second and Third Strands of about 8 to about 20 nucleosides.

A. Internucleoside Linkages

The Second and Third Strands of the present invention comprise optionally covalently linked Oligomers.

Oligomers having the desired internucleoside linkages may be conveniently prepared according to synthetic techniques known to those skilled in the art. For example, commercial machines, reagents and protocols are available for the synthesis of Oligomers having phosphodiester and certain other phosphorus-containing internucleoside linkages. See also Gait, M. J., *Oligonucleotide Synthesis: A Practical Approach*(IRL Press, 1984); Cohen, Jack S., *Oligodeoxynucleotides Antisense Inhibitors of Gene Expression*, (CRC Press, Boca Raton, Fla., 1989); and *Oligonucleotides and Analogues: A Practical Approach*, (F. Eckstein, ed., 1991). Preparation of Oligomers having certain non-phosphorus-containing internucleoside linkages is described in U.S. Pat. No. 5,142,047, the disclosure of which is incorporated herein by reference.

B. Nucleoside Bases

As set forth herein, the Second and Third Strands of the present invention may include certain analogues of the naturally occurring pyrimidine and purine bases. These analogs include the above-noted pyrimidine-5-donor/ acceptor bases. The synthesis of these bases used in our proposed binding motifs have been reported and by following those literature procedures, those bases can be made.

The ring structures for some of these bases and their abbreviations are set forth in FIG. 4.

In particular, the following bases may be prepared according to the following reported procedures.

The synthesis of pseudoisocytidine (ΨiC) is reported by Ono, A., et al., J. Org. Chem. 57:3225–3230 (1992).

The synthesis of 5-aza-cytidine ($^{5a}$C or pseudoisocytidine* or ΨiC*) is reported by Beisler, J. A., et al., J. Carbohyd. Nucleosides Nucleotides 4:281–299 (1977).

Pseudouridine (ΨU) is commercially available (from Kyowa Hakko Kogyo Co. Ltd., N.Y.).

The synthesis of pseudocytidine is reported by Pankiewicz, K. W., et al., Carbohyd. Res. 127:227–233 (1984).

The syntheses of 9-deaza-guanosine ($^{9deaza}$G or $^{9da}$G) and 9-deaza-inosine ($^{9deaza}$I or $^{9da}$I) are reported by Lim, et al., J. Org. Chem. 48:780–788 (1983).

The synthesis of 9-deaza-adenosine ($^{9deaza}$A or $^{9da}$A) is reported by Lim and Klein, Tetrahedron Letters 22:25–28 (1981).

The synthesis of isocytidine (iC) is reported by Switzer, C., et al., J. Am. Chem. Soc. 111:8322–8323 (1989).

Isoguanosine* (IG*) is synthesized by methods analogous to those reported by Revanker et al., J. Med. Chem. 27:1389 (1984) for 3-deazaguanine.

Inosine (I) and its phosphoramidite synthon are commercially available (from Cruachem, Herndon, Va.).

Inosine* (I*) and isoinosine* (iI*) may be prepared by methods analogous to those reported by Rosemeyer and Seela, J. Org. Chem. 52:5136–5143 (1987) for 5-aza-7-deazaguanosine.

Xanthine (X) and Xanthosine are commercially available (from Sigma).

The synthesis of 2-amino-purine ($^{2a}$p) is reported by McLaughlin, L. W., et al., Nucl. Acids Res. 16:5631–5644 (1988) and by Doudna, J. A., et al., J. Org. Chem. 55:5547–5549 (1990).

Second and Third Strand Complementarity

Preferred are Second and Third Strands that each have a corresponding nucleoside complementary to each nucleoside of the target sequence (i.e., have "exact complementarity"). However, included within the scope of the present invention are Second and Third Strands which may lack a complement for each nucleoside in the target sequence, provided that the Second Strand has such binding affinity for the target sequence and the Third Strand has sufficient binding affinity for the Second Strand that together the Second and Third Strands bind with the target sequence to recognize it or to inhibit its expression by forming a triple helix complex. Such strands are referred to as being "substantially complementary" or having "substantial complementarity".

The Second Strand should be substantially complementary to the target sequence and the Third Strand should be substantially complementary to the Second Strand in that there is sufficient hybridization and hydrogen-bonding between the strands for inhibition of expression of the target sequence, and if the target sequence is a portion of a mRNA, inhibition of translation, to occur. Sufficient hybridization and hydrogen-bonding is related to the strength of the hydrogen-bonding between bases as well as the specificity of the complementary strand. The strength of the hydrogen-bonding is influenced by the number and percentage of bases in a strand that are base paired to complementary bases, according to either Watson-Crick base pairing (for target-Second Strand binding) or between Second Strand and Third Strand, whether by previously described triplet formation schemes or by one of triad motifs I to V'. To be specific, the complementary bases of the strand must be sufficient in number so as to avoid non-specific binding to other sequences within a genome and while at the same time small enough in number to avoid non-specific binding between other sequences within a genome and portions of a long strand.

It will also be appreciated that the base sequence of either the Second or the Third Strand need not be 100 percent complementary to the sequence to which it is to bind. Preferably the sequence is at least about 80 percent complementary, more preferably at least about 90 percent and even more preferably about 95 percent or more. The Second and Third Strand may optionally include one or more non-nucleoside monomeric units. Such non-nucleoside monomeric units include those described in co-pending U.S. application Ser. No. 07/565,307, filed Aug. 9, 1990 (also published PCT Application No. WO 92/02532), the disclosure of which is incorporated herein by reference. The strand in question need only be capable of sufficient hybridization or bonding to the target sequence (or the Second Strand) to prevent or interfere with expression of the target sequence, such as by preventing normal translation of the target sequence or to specifically recognize the target sequence. Prevention of normal translation of the target sequence occurs when an expression product of the target sequence is produced in an amount significantly lower than would be the result in the absence of the Second and Third Strands. The expression product is a protein. Measurement of the decrease in production of proteins is well known to those skilled in the art and such methods include quantification by chromatography, biological assay or immunological reactivity.

Utility and Administration

According to the present invention, a specific segment of single stranded nucleic acid may be detected or recognized using Second and Third Strands which form a triple helix with the single stranded nucleic acid according to the triplet base pairing guidelines described herein. The Second and Third Strands have sequences selected as described above such that a base of the Second Strand will hydrogen bond with a base of the target sequence (by its Watson-Crick binding face) and with a corresponding base of the Third Strand (by its Second-Third Strand binding face) to give a triplet and, thus, to result in a triple helix complex. The Second and Third Strands are Oligomers which may be optionally covalently linked. Detectably labeled Oligomers may be used as proved for use in hybridization assays, for example, to detect the presence of a particular single-stranded nucleic acid sequence.

The present invention also provides a method of preventing or altering expression or function of a selected target sequence of single stranded nucleic acid by use of Second and Third Strands which form a triple stranded helix structure with the single stranded target as described above. Formation of the triple stranded helix may prevent expression and/or function by modes such as preventing transcription, preventing of binding of effector molecules (such as proteins), etc.

According to the methods of the present invention, a high affinity complex is formed with a high degree of selectivity. Derivatized Second and Third Strands may be used to detect or locate and then irreversibly modify the target site in the nucleic acid by cross-linking (psoralens) or cleaving one or both strands (EDTA). By careful selection of a target site for cleavage, one of the strands may be used as a molecular scissors to specifically excise a selected nucleic acid sequence.

The Second or Third Strands may be derivatized to incorporate a nucleic acid reacting or modifying group which can be caused to react with the nucleic acid segment or a target sequence thereof to irreversibly modify, degrade or destroy the nucleic acid and thus irreversibly inhibit its functions.

These Second and Third Strands may be used to inactivate or inhibit or alter expression of a particular gene or target sequence of the same in a living cell, allowing selective inactivation or inhibition or alteration of expression. The target sequence may be DNA or RNA, such as a pre-mRNA, an mRNA or an RNA sequence such as an initiator codon, a polyadenylation region, an mRNA cap site or a splice junction. These strands could then be used to permanently inactivate, turn off or destroy genes which produced defective or undesired products or if activated caused undesirable effects.

Another aspect of the present invention is directed to a kit for detecting a particular single stranded nucleic acid sequence which comprises Second and Third Strands at least one of which is detectably labeled and selected to be able sufficiently complementary to the target sequence of the single stranded nucleic acid to be able to form a triple helix structure therewith.

Since the Second and Third Strands for use with the methods of the present invention form triple helix complexes or other forms of stable association with transcribed regions, these complexes are useful in "antisense" therapy. "Antisense" therapy as used herein is a generic term which includes the use of specific binding Oligomers to inactivate undesirable DNA or RNA sequences in vitro or in vivo.

Many diseases and other conditions are characterized by the presence of undesired DNA or RNA, which may be in certain instances single stranded form and in other instances in double stranded form. These diseases and conditions can be treated using the principles of antisense therapy as is generally understood in the art. Antisense therapy includes targeting a specific DNA or RNA target sequence through complementarity or through any other specific binding means, in the case of the present invention by formation of triple helix complexes according to the binding motifs described herein.

The Oligomers for use in the instant invention may be administered singly, or combinations of Oligomers may be administered for adjacent or distant targets or for combined effects of antisense mechanisms with the foregoing general mechanisms.

In therapeutic applications, the Oligomers can be formulated for a variety of modes of administration, including systemic, topical or localized administration. Techniques and formulations generally may be found in *Remington's Pharmaceutical Sciences*, Mack Publishing Co., Easton, Pa., latest edition. The Oligomer active ingredient is generally combined with a carrier such as a diluent or excipient which may include fillers, extenders, binding, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection may be preferred, including intramuscular, intravenous, intraperitoneal, and subcutaneous. For injection, the Oligomers for use with the invention are formulated in liquid solutions, preferably in physiologically compatible buffers such as Hank's solution or Ringer's solution. In addition, the Oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucusal administration. In addition, detergents may be used to facilitate permeation. Transmucosal administration may be through use of nasal sprays, for example, as well as formulations suitable for administration by inhalation, or suppositories. For oral administration, the Oligomers are formulated into conventional oral administration forms such as capsules, tablets, and tonics.

For topical administration, the Oligomers for use in the invention are formulated into ointments, salves, eye drops, gels, or creams, as is generally known in the art.

In addition to use in therapy, the methods of the present invention may be used diagnostically to detect the presence or absence of the target DNA or RNA sequences to which the Oligomers specifically bind. Such diagnostic tests are conducted by hybridization through triple helix complex formation which is then detected by conventional means. For example, Oligomers may be labeled using radioactive, fluorescent, or chromogenic labels and the presence of label bound to solid support detected. Alternatively, the presence of a triple helix may be detected by antibodies which specifically recognize forms. Means for conducting assays using such Oligomers as probes are generally known.

We claim:

1. A method of detecting, recognizing and/or inhibiting or altering expression of a single stranded nucleic acid having a target sequence by binding Second and Third Strands which comprise Oligomers, said Oligomers being optionally covalently linked to each other and optionally containing non-nucleoside monomeric units, with the target sequence in a sequence specific manner to give a triple helix complex, said method comprising: (a) contacting said target sequence with Second and Third Strands whereby the Second Strand has a nucleoside base sequence which is sufficiently complementary to the target sequence to bind to the target sequence by Watson-Crick base pairing and the Third Strand has a nucleoside base sequence selected so as to hydrogen bond with and bind to the Second Strand in a sequence specific manner to form a triple helix complex therewith and wherein the Second Strand includes at least one nucleoside with a pyrimidine 5-donor acceptor base and the Third Strand has a corresponding nucleoside with a base capable of binding with said pyrimidine 5-donor acceptor base under physiological pH; and (b) whereby formation of the triple helix complex indicates the presence or identity of said single stranded nucleic acid; or (c) whereby formation of the triple helix complex results in the detection of inhibition or altered expression of said single stranded nucleic acid.

2. A method according to claim 1 wherein the nucleosides of the Third Strand are selected according to one of motifs I to V' of FIG. 2B.

3. A method according to claim 2 wherein the nucleosides of the Second Strand are selected according to one of permutations 1 to 4 of FIG. 2A.

4. A method of detecting, recognizing and/or inhibiting or altering expression of a single stranded nucleic acid having a target sequence by binding Second and Third Strands which comprise Oligomers, said Oligomers being optionally covalently linked to each other and optionally containing non-nucleoside monomeric units, with the target sequence in a sequence specific manner to give a triple helix complex said method comprising:

(a) contacting said target sequence with Second and Third Strands whereby the Second Strand has a nucleoside base sequence which is sufficiently complementary to the target sequence to bind to the target sequence by Watson-Crick base pairing and the Third Strand hydrogen bonds with and binds to the Second Strand in a sequence specific manner to form a triple helix complex therewith and wherein the Second Strand includes at least one nucleoside with a pyrimidine 5-donor/acceptor base and the Third Strand has a corresponding nucleoside with a base capable of binding with said pyrimidine 5-donor/acceptor base and wherein the nucleoside sequence of the Second Strand is selected according to one of permutations 1 to 4 of FIG. 2A and the nucleoside sequence of the Third Strand is selected according to one of motifs I to V' of FIG. 2B; and (b) whereby formation of said triple helix complex indicates the presence or identity of said single stranded nucleic acid; or (c) whereby formation of the triple helix complex results in the detection of inhibition or altered expression of said single stranded nucleic acid.

5. A method according to claim 4 wherein said Second and Third Strands comprise substantially neutral Oligomers.

6. A method according to claim 4 wherein said target sequence has from about 4 to about 40 nucleosidyl units.

7. A method according to claim 6 wherein said Second and Third Strands comprise substantially neutral Oligomers.

8. A method according to claim 7 wherein said substantially neutral Oligomers are methylphosphonate Oligomers.

9. A method of inhibiting or altering expression of a selected single stranded nucleic acid said method comprising:

(a) selecting a target sequence of said single stranded nucleic acid;

(b) contacting said target sequence with a Second and a Third Strand which comprise Oligomers, said Oligomers being optionally covalently linked to each other and optionally containing non-nucleoside monomeric units, wherein the Second Strand has a nucleoside base sequence which is substantially complementary to the target sequence and binds thereto and the Third Strand has a nucleoside base sequence which is substantially complementary to the Second Strand and wherein the Second Strand includes at least one nucleoside with a pyrimidine 5-donor/acceptor base and the Third Strand has a corresponding nucleoside with a base capable of binding with said pyrimidine 5-donor/acceptor base and wherein the nucleoside base sequence of the Second Strand is selected according to one of permutations 1 to 4 of FIG. 2A and the nucleoside sequence of the Third Strand is selected according to once of motifs I to V' of FIG. 2B; and (c) binding the Second Strand with both the target sequence and the Third Strand in a sequence specific manner to give a triple helix complex; and (d) whereby formation of the triple helix complex results in the detection of inhibition or altered expression of said single stranded nucleic acid.

10. A method according to claim 9 wherein said target sequence has from about 4 to about 40 nucleosides.

11. A method according to claim 10 wherein said Second and Third Strands comprise substantially neutral Oligomers.

12. A method according to claim 9 wherein said target sequence is a portion of a mRNA or a pre-mRNA.

13. A method of inhibiting or altering expression of a product of a selected mRNA, said method comprising contacting a target sequence of said mRNA or its pre-mRNA with a Second Strand and a Third Strand which strands comprise Oligomers, said Oligomers being optionally covalently linked to each other and optionally containing non-nucleoside monomeric units, wherein the Second Strand has a nucleoside base sequence selected to be substantially complementary to the target sequence according to one of permutations 1 to 4 of FIG. 2A and the Third Strand has a nucleoside base sequence selected to be substantially complementary to the Second Strand according to one of motifs I to V' of FIG. 2B whereby the Second and Third Strands form a triple helix complex in conjunction with the target sequence in a sequence specific manner and whereby formation of the triple helix complex results in the detection of inhibition or altered expression of said product of the selected mRNA.

14. A method according to claim 13 wherein the Second and Third Strands comprise about 4 to about 40 nucleosides.

15. A method according to claim 14 wherein the Second and Third Strands comprise substantially neutral Oligomers.

16. A triple helix complex formed by associating a Second Strand and a Third Strand which comprise Oligomers, said Oligomers being optionally covalently linked to each other and optionally containing non-nucleoside monomeric units, with a single stranded target sequence of a nucleic acid wherein the Second Strand includes at least one nucleoside with a pyrimidine 5-donor/acceptor base and the Third Strand has a corresponding nucleoside with a base capable of binding with said pyrimidine 5-donor/acceptor base and wherein the nucleoside base sequence for said Second Strand is selected to be substantially complementary to the target sequence according to one of permutations 1 to 4 of FIG. 2A and the nucleoside base sequence for the Third Strand is selected to be substantially complementary to the Second Strand according to one of motifs I to V' of FIG. 2B such that the Second Strand specifically and selectively associates by hydrogen bonding with the target sequence and the Third Strand in a sequence specific manner.

17. A method of detecting, recognizing or inhibiting or altering the expression of a specific target sequence of single stranded nucleic acid having nucleosides comprising both purine and pyrimidine bases, said method comprising:

(a) contacting the single stranded nucleic acid with a Second Strand and a Third Strand wherein said Second and Third Strands comprise Oligomers, said Oligomers being optionally covalently linked to each other and optionally containing non-nucleoside monomeric units, and the Second Strand has a nucleoside base sequence which is sufficiently complementary to said target sequence to bind thereto in a sequence specific manner and the Third Strand has a nucleoside base sequence which is sufficiently complementary to the Second Strand to form a triple helix complex by formation of triplets between bases of the target sequence and bases of each of the Second and Third Strands in a sequence specific manner and wherein the Second Strand comprises at least one nucleoside with a pyrimidine 5-donor/acceptor base; and (b) whereby formation of said triple helix complex indicates the presence or identity of said single stranded nucleic acid; or (c) whereby formation of the triple helix complex results in the detection of inhibition or altered expression of said single stranded nucleic acid.

18. A method according to claim 17 wherein the nucleoside sequence of said Second Strand is selected according to one of permutations 1 to 4 of FIG. 2A and the nucleoside sequence of the Third Strand is selected according to one of motifs I to V' of FIG. 2B.

19. A method of detecting, recognizing or inhibiting or altering expression of a single stranded nucleic acid having a selected target sequence, said method comprising forming a triple helix complex in a sequence specific manner between said target sequence, a Second Strand and a Third Strand by hydrogen bonding in a sequence specific manner between the target sequence and the Second Strand and between the Second Strand and the Third Strand, wherein (a) said Second Strand and Third Strand comprise Oligomers, said Oligomers being optionally covalently linked to each other and optionally containing non-nucleoside monomeric units; (b) said Second Strand has a nucleoside base sequence which is complementary to the target sequence; (c) said Third Strand has a nucleoside base sequence which is complementary to the Second Strand; (d) at least one nucleoside of the Second Strand has a pyrimidine-5-donor/acceptor base which has a Watson-Crick binding face which binds to a corresponding base of nucleoside of the target sequence by Watson-Crick base pairing and a Second-Third Strand binding face which specifically hydrogen bonds with a complementary base of a nucleoside of the Third Strand; and (e) whereby formation of the triple helix complex indicates the presence or identity of said single stranded nucleic acid; or (f) whereby formation of the triple helix complex results in the detection of inhibition or altered expression of said single stranded nucleic acid.

20. A method according to claim 19 whereby formation of the triple helix complex inhibits or substantially alters expression of the single stranded nucleic acid.

21. A method according to claim 20 wherein said target sequence comprises a portion of a mRNA or a pre-mRNA.

22. A method according to claim 19 wherein said Second and Third Strands comprise from about 4 to about 40 nucleosides.

23. A method according to claim 19 wherein the Second Strand has a nucleoside sequence selected according to one of permutations 1 to 4 of FIG. 2A and the Third Strand has a nucleoside sequence selected according to one of motifs I to V' of FIG. 2B.

24. A method according to claim 23 wherein the Second and Third Strands comprise from about 4 to about 40 nucleosides.

25. A method according to claim 24 wherein said Second and Third Strands comprise substantially neutral Oligomers.

26. A method of detecting, recognizing or inhibiting or altering expression of a single stranded nucleic acid having a selected target sequence of nucleosides comprising both purine and pyrimidine bases, said method comprising forming a triple helix complex in a sequence specific manner by sequence specific hydrogen bonding between the target sequence and a Second Strand and between the Second Strand and a Third Strand wherein (a) the Second Strand and Third Strand comprise Oligomers, said Oligomers being optionally covalently linked to each other and optionally containing non-nucleoside monomeric units; (b) the Second Strand includes at least one nucleoside with a pyrimidine 5-donor/acceptor base and the Third Strand has a corresponding nucleoside with a base capable of binding with said pyrimidine 5-donor/acceptor base, and the Second Strand has nucleosides wherein the base portion of each nucleoside has a Watson-Crick binding face and a Second-Third Strand binding face; (c) the nucleoside base sequence is selected so that the Watson-Crick binding face of each individual Second Strand nucleoside hydrogen bonds with a base of a corresponding nucleoside of the target sequence by Watson-Crick base pairing; and the Second-Third Strand binding face of each individual Second Strand nucleoside specifically hydrogen bonds with a complementary base of a corresponding nucleoside of the Third Strand; and (d) whereby formation of the triple helix complex indicates the presence or identity of said single stranded nucleic acid; or (e) whereby formation of the triple helix complex results in the detection of inhibition or altered expression of said single stranded nucleic acid.

27. A method of forming of a triple helix complex in a sequence specific manner between a target sequence of a single-stranded nucleic acid having any selected combination of pyrimidine and purine bases which comprises binding a Second Strand to the target sequence and a Third Strand to the Second Strand wherein the Second Strand includes at least one nucleoside with a pyrimidine 5-donor/acceptor base and the Third Strand has a corresponding nucleoside with a base capable of binding with said pyrimidine 5-donor/acceptor base and wherein the Second Strand has a nucleoside base sequence selected such that the base portions of the corresponding Second Strand nucleosides have Watson-Crick bonding faces possessing substantial complementarity to the base portions of corresponding nucleosides of the target sequence and Second-Third Strand binding faces possessing unique pairs of hydrogen binding sites so as to bind base portions of corresponding nucleosides of the Third Strand with substantial complementarity, thereby forming a triple helix.

28. A method according to claim 27 wherein said Second and Third Stands possess exact complementarity to each nucleoside of the target sequence.

29. A method of forming a triplet between a purine nucleoside of a target sequence of a single stranded nucleic acid, a corresponding nucleoside of a Second Strand and a corresponding nucleoside of a Third Strand and wherein the Second Strand nucleoside comprises a pyrimidine analog which has a Watson-Crick binding face capable of binding by Watson-Crick base pairing to the purine nucleoside of the target sequence and a Second-Third Strand binding face having at least two hydrogen bonding sites which specifically hydrogen bonds with the Third Strand nucleoside which comprises:

contacting the purine nucleoside of the target sequence with the Second Strand nucleoside and a Third Strand nucleoside which is complementary to the Second-Third Strand binding face to give a triplet.

30. A method according to claim 29 wherein said Third Strand nucleoside is selected according to one of motifs I to V' of FIG. 2B.

* * * * *